United States Patent
Kirkpatrick

(10) Patent No.: US 8,293,669 B2
(45) Date of Patent: Oct. 23, 2012

(54) BEVERAGE MANUFACTURE, PROCESSING, PACKAGING AND DISPENSING USING ELECTROCHEMICALLY ACTIVATED WATER

(75) Inventor: Robin Duncan Kirkpatrick, Johannesburg (ZA)

(73) Assignee: Radical Waters International Ltd. (VG)

( * ) Notice: Subject to any disclaimer, the term of this patent is extended or adjusted under 35 U.S.C. 154(b) by 301 days.

(21) Appl. No.: 12/366,735

(22) Filed: Feb. 6, 2009

(65) Prior Publication Data

US 2009/0203516 A1     Aug. 13, 2009

Related U.S. Application Data

(60) Provisional application No. 61/026,960, filed on Feb. 7, 2008.

(51) Int. Cl.
*B01J 20/34* (2006.01)
(52) U.S. Cl. .................................................. 502/22
(58) Field of Classification Search .................. None
See application file for complete search history.

(56) References Cited

U.S. PATENT DOCUMENTS

| | | | |
|---|---|---|---|
| 4,374,714 A | 2/1983 | Hekel | |
| 5,932,171 A * | 8/1999 | Malchesky | 422/29 |
| 6,391,185 B1 * | 5/2002 | Shvarev et al. | 205/687 |
| 6,521,810 B2 * | 2/2003 | Shapiro et al. | 204/555 |
| 2007/0243597 A1 * | 10/2007 | Kenyon et al. | 435/238 |
| 2009/0199866 A1 | 8/2009 | Kirkpatrick | |
| 2009/0199872 A1 | 8/2009 | Kirkpatrick | |
| 2009/0202661 A1 | 8/2009 | Kirkpatrick | |

FOREIGN PATENT DOCUMENTS

| | | |
|---|---|---|
| DE | 44 30 391 A1 | 2/1996 |
| WO | WO 03042112 A1 | 5/2003 |
| WO | WO 2004031337 A1 | 4/2004 |
| WO | WO 2009098599 A3 | 8/2009 |
| WO | WO 2007093395 A2 | 10/2009 |

OTHER PUBLICATIONS uhl et al, bacterial regrowth and disinfection byproduct removal in granular activated carbon filters in pool water treatment, 2005.*
camper et al, bacteria associated with granular activated carbon particles in drinking water, 1986, applied and environmental microbiology, vol. 52, No. 3, pp. 434-438.*

(Continued)

*Primary Examiner* — Melvin C Mayes
*Assistant Examiner* — Stefanie Cohen
(74) *Attorney, Agent, or Firm* — Fellers, Snider, Blankenship, Bailey & Tippens, P.C.; Dennis D. Brown

(57) ABSTRACT

A system using electrochemically-activated water (ECAW) for manufacturing, processing, packaging, and dispensing beverages including: (a) using ECAW to neutralize incompatible residues when transitioning from the production of one beverage to another; (b) using ECAW to rehabilitate and disinfect granular activated charcoal beds used in the feed water purification system; (c) producing a carbonated ECAW product and using the carbonated ECAW for system cleaning or disinfecting; (d) using ECAW solutions in the beverage facility clean-in-place system to achieve improved microbial control while greatly reducing water usage and reducing or eliminating the use of chemical detergents and disinfectants; (e) further reducing biofilm growth in the processing system, and purifying ingredient water without the use of chlorine, by adding an ECAW anolyte to the water ingredient feed stream; and/or (f) washing the beverage product bottles or other packages with one or more ECAW solutions prior to packaging.

9 Claims, 11 Drawing Sheets

OTHER PUBLICATIONS

Brauwelt International, "Optimized Hygiene in the Beverage Filling Process", 2009, pp. 300-302, vol. 2009, No. V, Published in: US.

Uhl, Hartmann, Kreckel, "Bacterial Regrowth and Disinfection Byproduct Removal in Granular Activated Carbon Filters in Pool Water Treatment",, Published in: US, 2007.

Uhl & Hartmann, "Disinfection by-products and microbial contamination in the treatment of pool water with granular activated carbon",, Published in: US, 2005.

* cited by examiner

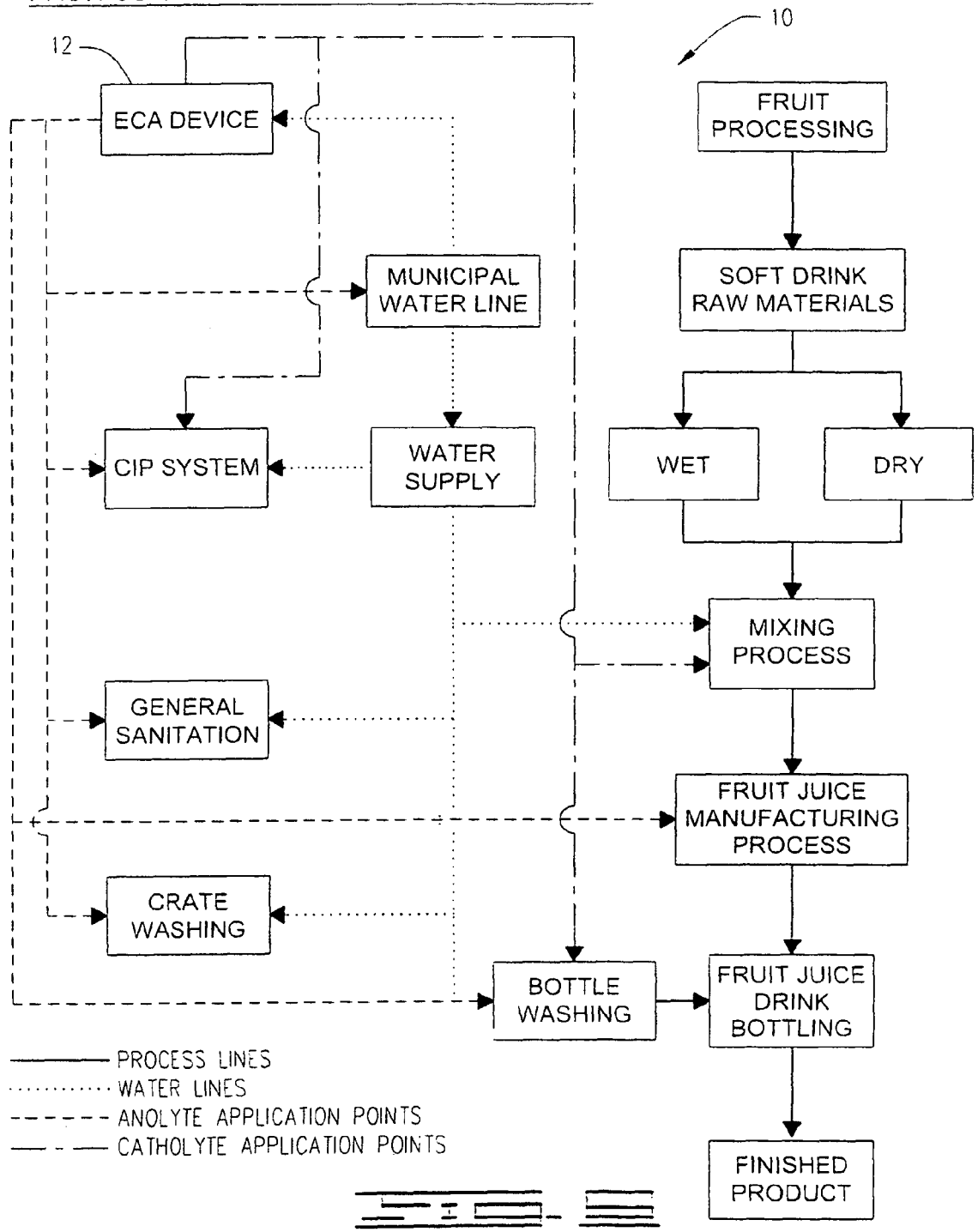

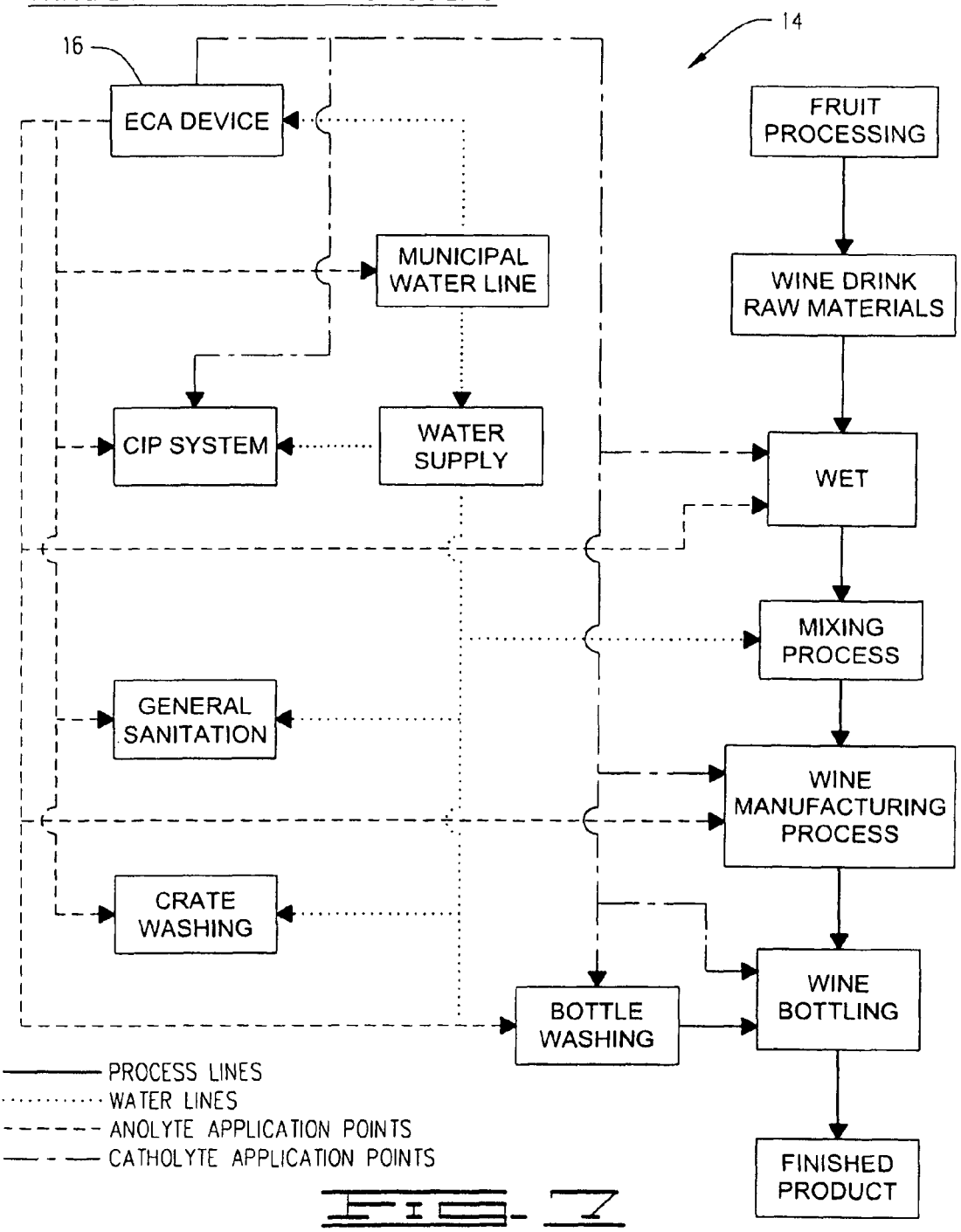

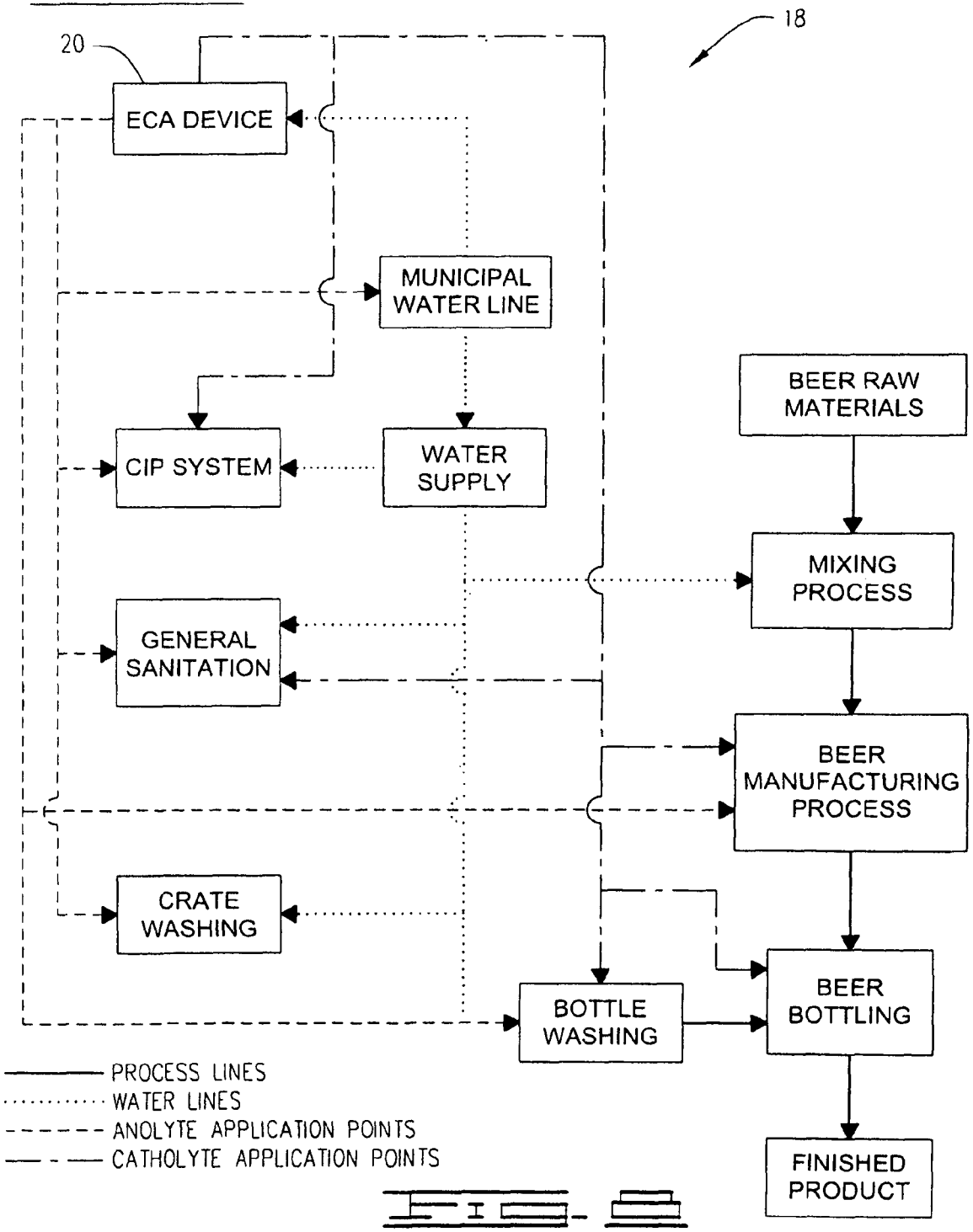

BEVERAGE MANUFACTURE, PROCESSING, PACKAGING AND DISPENSING USING ELECTROCHEMICALLY ACTIVATED WATER

This application claims the benefit of U.S. Provisional Patent Application Ser. No. 61/026,960 filed on Feb. 7, 2008 and incorporates said provisional application by reference into this document as if fully set out at this point.

FIELD OF THE INVENTION

This invention relates to the use of, and to products produced by the use of, electrochemically activated (ECA) water during the production, processing, packaging (e.g., bottling, canning, etc.), and/or dispensing of water, fruit juice, carbonated soft drinks, sports drinks, fermented beverages, brewed beverages, and other beverages.

BACKGROUND OF THE INVENTION

Beverage Processing and Packaging

It is well established within beverage production and packaging facilities that highly sanitary conditions, and effective protocols therefor, must be maintained in order to satisfy internal quality assurance requirements and meet batch release specifications.

With progressively more diverse beverage types being developed, manufactured, and packaged within the same facility using the same production lines, the pressure to increase productivity and still accommodate the reliable supply of an expanding number of different product varieties necessitates effective cleaning and disinfecting strategies to prevent microbial contamination and to prevent the carryover of residual contaminating ingredients (e.g., flavors, colors, alcohol content, etc.) between different batches and product types.

Given that most beverage manufacturing and packaging equipment is part of a permanent installation (i.e., the individual system components cannot conveniently be removed and separately treated), the cleaning and disinfection thereof requires the introduction and circulation of dedicated agents throughout the entire system, rather than allowing specific individual interventions which would necessitate that the equipment be disassembled and manually cleaned and disinfected. "Cleaning-in-Place" (CIP) thus refers to the practice of circulating cleaning and disinfecting agents throughout the entire assembly of system components, equipment, and subsystems. "Cleaning-out-Place" (COP), on the other hand, refers to those procedures wherein disassembled equipment and removable fixtures are cleaned and disinfected separately and largely by hand at stations away from the permanent manufacturing and packaging systems.

The diverse products that are prepared and packaged within the same facility using the same filling equipment can often even comprise both alcoholic and non-alcoholic products. The packaging conditions for all such products is governed by the same stringent cleaning and disinfection prescriptions that are mandated to preclude cross contamination that would apply between highly flavorful and odor intense products and bottled water. Optimal removal of these robust flavors or alcoholic residues remains a primary limitation to the quick cleaning and turn-around of the filling line and contributes to the large amount of water typically consumed during line and filler head cleaning when switching between incompatible and non-benign products.

Aside from the ubiquitous likelihood of microbial contamination and the associated potential for product spoilage and deterioration, further product quality criteria that must comply with internal batch release specifications include color, taste, smell, and overall character such as foaming ability and beverage consistency.

Conventional measures heretofore used to address these concerns and limitations have comprised: the use of solutions or remedies heated to substantially elevated temperatures; the use of increased liquid and gaseous pressures; the use of high fluid circulation rates; and extended exposure to high concentrations of caustic detergents and potentially hazardous biocidal compounds.

However, these measures, whilst being largely effective for cleaning and sanitation, remain substantially deficient in terms of (a) the loss of productivity resulting from the current inability in the industry to quickly switch the processing line from one product to another and (b) the high energy, potable water, and labor demands of the prior procedures. In addition to controlling the high cost of other items in the manufacture and packing process, water consumption also remains a pivotal criterion for production efficiency measurement and management.

Besides the cleaning and sanitization procedures discussed above, further measures are typically used to ensure the quality of process and ingredient water used in beverage processing plants. Such procedures include a variety of filtration technologies including the use of synthetic membranes of varying porosities and the use of Granular Activated Charcoal (GAC) beds or columns for the 'scrubbing' of partially processed water to achieve selective removal of hazardous pesticides and fungicides, toxins, inorganic compounds, and organic residues or contaminants.

Unfortunately, any filtration technology, whether membrane based and/or GAC in type, will continuously trap the agents or elements that are being filtered. These filtrates progressively accumulate to the point that the selective separation efficiency of the system is compromised. The maintenance and rejuvenation of these fouled filtration systems has thus heretofore required either (a) costly and largely non-environmentally friendly intermittent replacement of the core filtration components or (b) physical (heat) and/or chemical interventions to rehabilitate and restore the systems to functional efficiency The discharge of large volumes of soiled effluent solutions (e.g., effluents containing beverage ingredients, disinfectants, cleaning chemicals, etc.) into waste water reticulation systems is also an important environmental constraint to optimal beverage production and packaging capacity. Steps to limit the amounts of CIP chemicals and/or beverage contaminants in the effluent streams include the installation of systems to recover and store the different chemical agents for re-use, as well as efforts to limit the amount of rinse water used to remove the chemical residues from the diverse systems after cleaning and disinfection. While more efficient and judicious water and chemical usage provides a degree of improvement in the quantity and quality of the effluent discharge, the quality and quantity of the effluent discharge continues to constitute a critical production constraint in beverage manufacturing and packaging facilities.

Aside from the need to enhance the degree of efficiency and quality compliance achieved during the manufacture and packaging of beverage products, it is also critical to the maintenance of final product integrity that due effort be invested in ensuring that beverage dispensing systems (e.g., water and soda fountains and draft beer dispensers) be similarly cleaned of residual product and disinfected. Product residues serve as a medium for further microbial growth and, thus, biofilm development, and have an adverse impact upon dispensed product quality, health, and safety.

Consequently, in a production environment where there is a great deal of pressure to optimize the productivity of existing fixed assets (i.e., processing and packaging lines, etc.) and where there is a progressively heightened consumer and shareholder awareness and disapproval of the inefficient usage of resources, a great need exists for a more holistic and progressively renewable approach to cleaning and sanitation in order to realize sustainable quality assurance and enhanced productivity.

Electrochemically Activated Water (ECA)

It is well known that electrochemically activated (ECA) water can be produced from diluted dissociative salt solutions by passing an electrical current through the electrolyte solution in order to produce separable catholyte and anolyte products. The catholyte, which is the solution exiting the cathodal chamber, is an anti-oxidant which typically has a pH in the range of from about 8 to about 13 and an oxidation-reduction (redox) potential (ORP) in the range of from about −200 mV to about −1100 mV. The anolyte, which is the solution exiting the anodal chamber, is an oxidant which typically has a pH in the range of 2 to about 8, an ORP in the range of +300 mV to about +1200 mV and a Free Available Oxidant (FAO) concentration of $\leq 300$ ppm.

During electrochemical activation of aqueous electrolyte solutions, various oxidative and reductive species can be present in solution, for example: HOCl (hypochlorous acid); $ClO_2$ (chlorine dioxide); $OCl^-$ (hypochlorite); $Cl_2$ (chlorine); $O_2$ (oxygen); $H_2O_2$ (hydrogen peroxide); $OH^-$ (hydroxyl); and $H_2$ (hydrogen). The presence or absence of any particular reactive species in solution is predominantly influenced by the derivative salt used and the final solution pH. So, for example, at pH 3 or below, HOCl tends to convert to $Cl_2$, which increases toxicity levels. At a pH below 5, low chloride concentrations tend to produce HOCl, but high chloride concentrations typically produce $Cl_2$ gas. At a pH above 7.5, hypochlorite ions ($OCl^-$) are typically the dominant species. At a pH>9, the oxidants (chlorites, hypochlorites) tend to convert to non-oxidants (chloride, chlorates and perchlorates) and active chlorine (i.e. defined as $Cl_2$, HOCl and $ClO^-$) is typically lost due to conversion to chlorate ($ClO_3^-$). At a pH of 4.5-7.5, the predominant species are typically HOCl (hypochlorous acid), $O_3$ (ozone), $O_2^{2-}$ (peroxide ions) and $O^{2-}$ (superoxide ions).

For this reason, anolyte will typically predominantly comprise species such as ClO; $ClO^-$; HOCl; $OH^-$; $HO_2$; $H_2O_2$; $O_3$; $S_2O_8^{2-}$ and $Cl_2O_6^{2-}$, while catholyte will typically predominantly comprise species such as NaOH; KOH; Ca$(OH)_2$; Mg$(OH)_2$; $HO^-$; $H_3O_2^-$; $HO_2^-$; $H_2O_2^-$; $O_2^-$; $OH^-$ and $O_2^{2-}$. The order of oxidizing power of these species is: HOCl (strongest)>$Cl_2$>$OCl^-$ (least powerful). For this reason, anolyte has a much higher antimicrobial and disinfectant efficacy in comparison to that of catholyte, or of commercially available stabilized chlorine formulations used at the recommended dosages.

SUMMARY OF THE INVENTION

The present invention satisfies the needs and alleviates the problems discussed above. The benefits of the invention include, but are not limited to: microbial decontamination; reducing or eliminating the need for harmful cleaning and disinfection chemicals; biocide potentiation; elimination of pesticide contaminants; and odor and flavor residue neutralization, in the processed, packaged and/or dispensed product, the processing infrastructure, and the packaging containers.

In one aspect, there is provided a method of transitioning at least a portion of a beverage processing system from processing a first beverage to processing a second beverage wherein the first beverage includes a material which is not compatible with the second beverage and an amount of material remains in the beverage processing system after processing the first beverage. The material can be a substance which imparts a flavor, a substance which imparts a color, an alcohol, a substance which imparts a smell, or a combination thereof. The method comprises the steps of: (a) delivering an amount of an electrochemically-activated water anolyte solution through the portion of the beverage processing system effective for oxidizing at least a portion of the material therein and then (b) processing the second beverage in the portion of the beverage processing system. The portion of the material oxidized by the electrochemically-activated water anolyte solution in step (a) is an amount sufficient such that the material will not prevent the second beverage from meeting a release requirement for taste, smell, color, alcohol content, or a combination thereof. The electrochemically-activated water anolyte solution can be used in step (a) in undiluted form or can be delivered through the portion of the beverage processing system in step (a) as an aqueous dilution of the electrochemically-activated water anolyte solution.

As used herein and in the claims, the term "beverage processing system" refers to the entire production and packaging system for any given beverage. The entire system can comprise an assembly of numerous different portions including all lines and subsystems for producing and packaging the product. Examples of such lines and subsystems include, but are not limited to, ingredient delivery systems, ingredient mixing systems, fill lines for filling bottles or other packages and intermediate processing systems for heating, cooling, or carbonation, and/or subsystems for conducting other production procedures.

In another aspect, there is provided a method comprising the use of a non-toxic ECAW (preferably the catholyte or an aqueous catholyte dilution) as a cleaning agent for the removal of residual beverage soils from beverage production and packaging equipment. This cleaning agent may be included in the clean-in-place (CIP) procedure at ambient temperatures and, relative to conventional alkaline caustic soda based cleaning formulations, the ECAW is substantially free-rinsing, thus obviating the need for a mandatory large-volume, post-caustic water rinse. Thus, in a further aspect of the invention, the inventive method enhances water efficiency. Also in this regard, the intrinsic compatibility of the catholyte solution used for cleaning with the oxidant anolyte solution used for terminal disinfection permits the sequential and tandem application of the two solutions (catholyte and then anolyte) without the need for an intermediate rinse step. The disinfecting properties of the anolyte solution are not compromised by residual catholyte carry-over.

In another aspect, there is provided a method comprising the use of electrochemically activated water (ECAW) (preferably anolyte or an aqueous anolyte dilution) as a non-toxic disinfecting remedy in the production and packaging of diverse beverages types. The ECAW preferably includes HOCl, which is more effective at killing harmful pathogens than hypochlorite. This remedy also has the advantage of being substantially effective at ambient temperatures and obviates the need for high temperature manipulations of the disinfectant wash solutions to achieve equivalent levels of microbial control.

In another aspect, there is provided an improved process for cleaning-in-place at least a portion of a beverage processing system wherein the process uses an overall total volume of water and the process has comprised the steps of (a) delivering an amount of an aqueous rinse through the portion of the beverage processing system and then (b) delivering an amount of an aqueous disinfectant solution through the portion of the beverage processing system, the amount of the aqueous rinse and the amount of the aqueous disinfectant solution together being effective to attain a level of microbial control therein. The improvement comprises reducing the overall total volume of water used in the process and reducing the amount of the aqueous disinfectant solution used in step (b) while still obtaining at least the same level of microbial control. This is achieved by using an electrochemically-activated water anolyte solution as the aqueous disinfectant solution in step (b).

In another aspect of the inventive clean-in-place process, the inventive improvement preferably also comprises further reducing the overall total volume of water used in the process and reducing the amount of the aqueous rinse used in step (a) while still obtaining at least the same level of microbial control. This is achieved by using an aqueous electrochemically-activated water anolyte dilution as the aqueous rinse in step (a).

Examples of beverage processing systems wherein the improved clean-in-place process can be used include, but are not limited to, systems for processing carbonated soft drinks, brewed beverages, fruit beverages, fermented beverages, vegetable beverages, sport drinks, coffee beverages, tea beverages, or combinations thereof. As another example, the improved clean-in-place process can also be used in beverage processing systems for providing bottled or packaged water.

In another aspect, there is provided an improved process for cleaning-in-place at least a portion of a beverage processing system wherein the process uses an overall total volume of water and the process has comprised the steps of (a) delivering an amount of an aqueous cleaning solution through the portion of the beverage processing system, then (b) delivering an amount of an intermediate aqueous rinse through the portion of the beverage processing system, and then (c) delivering an amount of an aqueous disinfecting solution through the portion of the beverage processing system, wherein the amount of the aqueous cleaning solution, the amount of the intermediate aqueous rinse, and the amount of the aqueous disinfecting solution together have been effective to obtain a level of microbial control in the portion of the beverage processing system. The improvement comprises reducing the overall total volume of water used in the process and reducing the amount of the aqueous cleaning solution used in step (a) and the amount of aqueous disinfecting solution used in step (c) while still obtaining at least the same level of microbial control. This is achieved by: (i) using an electrochemically-activated water catholyte solution as the aqueous cleaning solution in step (a); (ii) using an electrochemically-activated water anolyte solution as the aqueous disinfecting solution in step (c); and (iii) reducing the amount of or eliminating the intermediate aqueous rinse in step (b).

In another aspect, there is provided a method of rehabilitating and disinfecting a Granular Activated Charcoal (GAC) bed used for purifying water. The method comprises the non-simultaneous steps of: (a) contacting the GAC bed with an electrochemically-activated water catholyte solution and (b) contacting the GAC bed with an electrochemically-activated water anolyte solution.

In the method of rehabilitating and disinfecting a GAC bed, the electrochemically-activated water anolyte solution will have a beginning oxidation-reduction potential prior to contacting the GAC bed and will have a spent oxidation-reduction potential after being used for contacting the bed. The beginning oxidation-reduction potential of the electrochemically-activated water anolyte solution will preferably be a positive mV oxidizing value. In addition, step (b) of the method preferably comprises the steps of: (i) determining the beginning oxidation-reduction potential of the electrochemically-activated water anolyte solution, (ii) contacting the GAC bed with the electrochemically-activated water anolyte solution, (iii) determining the spent oxidation-reduction potential of the electrochemically-activated water anolyte solution after step (ii), and (iv) repeating steps (ii) and (iii) at least until the spent oxidation-reduction potential of the electrochemically-activated water anolyte solution determined in step (iii) is a positive mV oxidizing value which is not more than 544 mV less than the beginning oxidation-reduction potential prior to step (ii). More preferably, in step (iv), steps (ii) and (iii) will be repeated at least until the spent oxidation-reduction potential of the electrochemically-activated water anolyte solution is not more than 143 mV, most preferably not more than 104 mV, less than the beginning oxidation-reduction potential.

In addition, step (ii) of the method for rehabilitating and disinfecting a GAC bed is preferably conducted at least twice such that: (1) the electrochemically-activated water anolyte solution is at least once delivered to the GAC bed in a substantially normal operating flow direction and (2) the electrochemically-activated water anolyte solution is at least once delivered to the GAC bed in a reverse flow direction which is substantially opposite the substantially normal operating flow direction. Similarly, step (a) of the method for rehabilitating and disinfecting a GAC bed is also preferably conducted at least twice such that (1) the electrochemically-activated water catholyte solution is at least once delivered to the GAC bed in a substantially normal operating flow direction and (2) the electrochemically-activated water catholyte solution is at least once delivered to the GAC bed in a reverse flow direction which is substantially opposite the substantially normal operating flow direction.

In another aspect, there is provided a method of treating Granular Activated Charcoal (GAC) columns used in beverage production, or in non-beverage systems, for the filtration of process water and the adsorption of noxious impurities and chemical contaminants. In the inventive method, the rehabilitation and regeneration of the carbon granules is preferably achieved by the strategic tandem introduction of ECA solutions as a substitute, or at least as a supplement, for conventional thermal or chemical regeneration procedures.

In another aspect, there is provided a method of disinfecting Granular Activated Charcoal (GAC) filtration systems wherein the contaminated adsorption surfaces within the pores of the carbon granules are exposed to an ECAW oxidant solution (preferably anolyte or an aqueous anolyte dilution) which facilitates both (a) the removal of microbial colonies and established biofilm, and (b) the elimination of both sessile and planktonic microbe species within the GAC system. The inventive method reduces or eliminates the need for noxious chemical, high temperature, and pressurized steam interventions of the type heretofore used for sanitizing such systems.

In another aspect, there is provided a method of predicting the biocidal performance of the ECA solutions whilst circulating in a GAC system by measuring the physio-chemical attributes of both the influent and effluent streams of the ECA treatment solution. By this method, the rate of ECA solution replenishment relative to the residual surface charge will afford a relative correlate to the measure of Oxidant Reduction Potential (ORP), and hence the volume of each specific ECA solution that will need to be applied to the GAC system in order to effect optimal biofilm removal and microbial elimination and to regenerate adsorption capacity of the GAC system.

In another aspect, there is provided a method comprising the in-process introduction of food-grade, aqueous-based ECAW biocide for use during the manufacture and packaging of beverage products, the method being particularly effective for the terminal control of superficial microbial biofilm growth, this with a resultant reduction of recontamination of packaged product from the same biofilm associated spoilage and pathogenic microbes.

In another aspect, there is provided a method of at least reducing biofilm growth in a beverage processing system having a water ingredient feed stream. The method comprises the step of adding an electrochemically-activated water anolyte solution to the water feed stream in an amount not exceeding 20 parts by volume of the electrochemically-activated water anolyte solution per 80 parts by volume of the water ingredient feed stream.

In another aspect, there is provided an improved process for producing a beverage product wherein the process includes placing the beverage product in product packages. The improvement comprises the step, prior to placing the beverage product in the packages, of washing the product packages using an electrochemically-activated water catholyte solution. The product packages treated in accordance with this process can be bottles or other types of containers. The improvement also preferably comprises the step, prior to the step of washing, of spraying, soaking, or otherwise contacting the product packages in an electrochemically-activated water anolyte solution.

In another aspect, there is provided a method of potentiating an electrochemical property (e.g., pH, oxidation-reduction potential, free active oxidant content, and/or electrical conductivity) of an electrochemically-activated water solution comprising the step of dissolving $CO_2$ in the electrochemically-activated water solution to produce a carbonated product solution. The electrochemically-activated water solution can be an anolyte solution, a catholyte solution, or a combination thereof and can be in undiluted or in aqueous dilution form.

In another aspect, there is provided a carbonated composition comprising an electrochemically-activated water solution having an effective amount of $CO_2$ dissolved therein to produce a positive mV change in an oxidation-reduction potential of the electrochemically-activated water solution. The electrochemically-activated water solution can be an anolyte solution, a catholyte solution, or a combination thereof and can be either in undiluted form or in the form of an aqueous dilution.

In another aspect, there is provided a method cleaning or disinfecting at least a portion of a food processing system comprising the step of treating the portion of the food processing system with a carbonated solution comprising an electrochemically-activated water solution having an effective amount of $CO_2$ dissolved therein to produce a positive mV change in an oxidation-reduction potential of the electrochemically-activated water solution. The electrochemically-activated water solution can be an anolyte solution, a catholyte solution, or a combination thereof and can be in undiluted or in aqueous dilution form.

In another aspect, there is provided a method to potentiate the biocidal activity of an oxidant ECA solution comprising the introduction of gaseous carbon dioxide ($CO_2$) into the ECAW or diluted ECAW to carbonate or pressurize the ECA solution. Thus, there is also provided a method comprising the introduction of carbonated ECAW, or a carbonated aqueous dilution of ECAW, into the production, processing and packaging system and infrastructure and/or elsewhere in the beverage production and packaging system, or into a non-beverage system. Using REDOX potential (ORP) as a reliable predictor of biocidal activity, it has been discovered in accordance with the present invention that, with the use of a carbonated ECA solution, a reduced amount and/or rate of ECAW is needed, when contrasted with non-carbonated oxidant ECA solutions, to achieve a given level of antimicrobial efficacy.

The specific introduction of $CO_2$ during the disinfection of the beverage mixing and filling equipment additionally serves to assure optimal disinfection by increasing the exposure of the "$CO_2$ potentiated oxidant" to all aspects of the filling and mixing equipment. Conventional pressure gradients driven by supply pumps within the beverage filler equipment may not afford adequate disinfectant distribution efficiency for optimal antimicrobial effect.

The surprising and unexpected increase in potency of aqueous dilute anolyte solutions which have been "carbonated" with $CO_2$ allows the amount of anolyte used in any particular application to be reduced without compromising antimicrobial activity. One benefit of this discovery is the further minimization of any potential adverse impact that the anolyte might have when used in conjunction with high risk, ultra sensitive products such as bottled water and preservative-formulations such as iced coffee wherein taste, color, and consistency are critical elements of the product's constitution.

The carbonation of water-based beverages with $CO_2$ gas typically results in the formation of an amount of carbonic acid ($H_2CO_3$). It is believed that the increased disinfecting potency of the inventive carbonated anolyte may, to some extent, result from the formation of an amount of carbonic acid in the carbonated aqueous anolyte solution.

In yet another aspect, there is provided a method comprising treating beverage production and packaging equipment with ECAW or aqueous diluted ECAW at ambient temperatures to neutralize the residual odor and taste of flavorant ingredients that conventionally require both protracted exposure to high temperature caustic detergent solutions and extended water rinse cycles.

In another aspect, there is provided an ECAW solution, and a method comprising the application of the ECAW solution, for the improved removal and elimination of alcohol-containing residues from beverage production systems, containers, and packaging system infrastructure.

In another aspect, there is provided a method of using ECAW as a cleaning agent, a sanitizing agent, and/or an ingredient in the production, processing, and packaging of beverages of all types. The method eliminates chemical pesticide, fungicide and herbicide residues which may be harmful to the integrity of the beverage and the health of the consumer. Such residues are common contaminants in process water supplies deriving, for example, from areas of high agricultural activity and pose a significant health and safety risk.

In another aspect, there is provided a method, and an ECAW solution therefor, wherein the ECAW solution enhances the antimicrobial biosecurity of intermediate and pre-packaged products which may be subjected to unplanned transient or extended in-process storage where unchecked microbial growth would adversely impact upon final product quality.

In another aspect, there is provided a method wherein ECAW is used for the safe and effective cleaning and decontamination of beverage dispensing systems including, but not limited to, water and soda fountains and draft beer dispensing systems.

Further objects, features, and advantages of the present invention will be apparent to those of ordinary skill in the art upon examining the accompanying drawings and upon reading the following detailed description of the preferred embodiments.

BRIEF DESCRIPTION OF THE DRAWINGS

FIG. 3 is a chart showing microbial count results obtained in Example 1 for the final rinse wash.

FIG. 6 is a flow diagram illustrating an embodiment 10 of an improved fruit juice production and packaging system provided by the present invention.

FIG. 7 is a flow diagram illustrating an embodiment 14 of an improved wine production and bottling system provided by the present invention.

FIG. 8 is a flow diagram illustrating am embodiment 18 of an improved beer production and packaging system provided by the present invention.

DETAILED DESCRIPTION OF THE PREFERRED EMBODIMENTS

Figure 1:
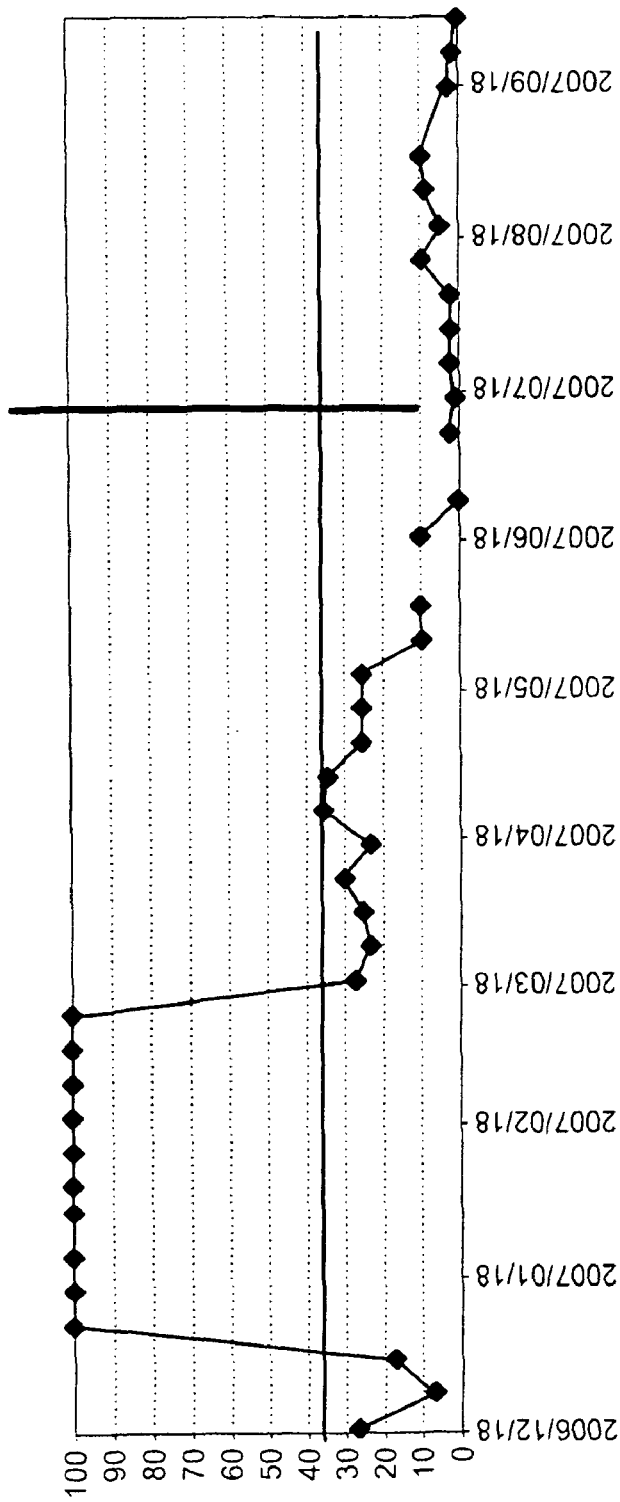
FIG. 1 is a chart showing microbial count results obtained in Example 1 for packaged product.

According to the invention, there is provided an in-process, real-time method of biocide intervention wherein ECAW (i.e., anolyte, catholyte, or a combination thereof) is used as a disinfectant and/or detergent during the production, packaging and/or dispensing of a diverse range of beverage products. The inventive method is capable of producing intermediate products and packaged final products which consistently meet stringent sanitary specifications.

In one aspect, the inventive method preferably comprises the step of sanitizing the beverage production and/or packaging systems for intermediate and packaged products (including either (a) substantially the entire production line/system, (b) any desired portion thereof, or (c) any selected subsystems) by delivering through the system(s) an electrochemically activated aqueous anolyte, or an aqueous dilution thereof. The anolyte used preferably has a pH (undiluted) in the range of from about 4.5 to about 7.5, an ORP (undiluted) in the range of from about +650 mV to $\geq$+900 mV, and a free available oxidant (FAO) concentration (undiluted) of $\leq$300 ppm. The pH (undiluted) of the anolyte will more preferably be in the range of from about 5.5 to about 7.

The anolyte, when added to or delivered through the various phases of the process (filtration, sanitization, and ingredient water), will have and will impart distinctive physiochemical attributes such as pH, electrical conductivity, ORP and Free Available Oxidant (FAO) concentration. These parameters, in turn, have a direct causal relationship with antimicrobial efficacy based upon an inverse relationship between microbial bioload and anolyte dilution applied. In other words, higher microbial counts require either (a) a higher anolyte concentration (i.e., lower dilution) for a shorter exposure time or (b) a longer exposure period for a lower anolyte concentration (i.e., greater dilution). This reflects the fact that there is a direct correlation between the measure of the aqueous dilution of the anolyte and the predictable changes in the Electrical Conductivity and Free Available Oxidant concentration being measured in the diluted sample. The pH and ORP changes within the dilution series do not follow identical linear reduction trends. The ORP values tend to remain substantially elevated until highly: diluted (1:50-1:100), at which point the ORP falls dramatically. pH, on the other hand, tends to remain constant and to assume the pH value of the diluent water.

These parameters can be measured on a real-time basis so as to reliably predict the antimicrobial capacity of the anolyte solution at any given point. There is a direct correlation between ORP and predictable antimicrobial activity. High ORP (i.e. $\geq$600 mV) will yield effective microbial elimination within 5 minutes. This efficacy falls, however, when the ORP is reduced. At low ORP anolyte concentrations and/or high microbe levels, antimicrobial activity can be increased as needed by increasing the exposure time.

The anolyte will preferably be produced by electrochemically activating a dilute aqueous saline solution comprising in the range of from about 1 to about 9 grams of salt per liter of water. The saline solution will preferably comprise from about 2 to about 3 grams of salt per liter of water.

The salt can be any inorganic salt. The salt will preferably be non-iodated sodium chloride (NaCl) or potassium chloride (KCL).

The inventive method can include the step of generating the anolyte solution on site. Various types of equipment and procedures which can be used to produce anolyte having the characteristics described above are known in the art. As will be understood by those in the art, a preferred procedure comprises the steps of: electrochemically activating a dilute electrolyte (salt) solution in an electrochemical reactor comprising anodal and cathodal chambers from which separable electrochemically activated aqueous anolyte and catholyte solutions (i.e., the "concentrated solutions") can be produced; separately harvesting the catholyte solution; reintroducing at least some of the catholyte solution into the anodal chamber in the absence of any fresh water; and manipulating the flow rate, hydraulic flow configuration and regimen, pressure and temperature of the catholyte through the anodal chamber as needed so as to produce an anolyte solution that is characterized in that it predominantly includes the species HOCl (hypochlorous acid), $O_3$ (ozone), $O_2^{2-}$ (peroxide ions) and $O_{2-}$ (superoxide ions), and has a Free Available Oxidant (FAO) concentration of $\leq$300 ppm.

When used in the inventive method as a sanitizing wash for beverage production, processing, and packaging systems, the anolyte will preferably be diluted with water. The diluted anolyte solution will preferably comprise at least 50 parts by volume of water per 50 parts by volume of concentrated anolyte. More preferably, the diluted anolyte will have a water-to-anolyte volume ratio of at least 60:40 when used in systems for producing and packaging manufactured beverages such as carbonated soft drinks and brewed beverages, and will have a water-to-anolyte ratio of at least 50:50 in systems for producing and packaging fruit based or fermented fruit or vegetable based products. In each case, the parts by volume ratio of water to concentrated anolyte will preferably not be greater than 98:2, will more preferably not be greater than 95:5, will more preferably be in the range of from about 94:6 to about 60:40, and will most preferably be in the range of from about 93:7 to about 65:35.

The anolyte sanitizing wash can desirably be introduced at a temperature as per standard operating conditions. The anolyte sanitizing wash will preferably be introduced at a temperature in the range of from about 5° C. to about 45° C.

The inventive method can comprise continuous and/or episodic treatment interventions by introduction of the anolyte solution at single and/or multiple sanitation points or sections of the beverage system so as to maintain the Oxidation-Reduction Potential (ORP) of the anolyte solution at desired levels throughout the system being treated, this to further ensure that the predictive relationship between the minimum microbiocidal and measured oxidant reactivity of the anolyte sanitizing wash is maintained throughout the system during sanitation.

The inventive method can also include a further step of selectively administering an anti-oxidant, electrochemically activated aqueous catholyte solution into the beverage production, processing, and/or packaging system as a free rinsing detergent or surface active agent. The period of exposure required is well within the time constraints of high volume processing and packaging. The catholyte (undiluted) will preferably have a pH in the range of from about 8 to about 13 and a negative ORP of at least −700 mV.

The inventive method can further include the step of washing any desired aspect of the beverage system with an anolyte having a pH (undiluted) in the range of from about 2 to about 5 and an ORP (undiluted) of ≧1000 mV. This distinctive anolyte solution can be applied at any appropriate treatment point in the beverage system. Examples of particularly beneficial treatment points include, but are not limited to, bulk holding vessels, fermentation vats, bright beer or synthetic syrup tanks, transfer vessels, and/or allied reticulation systems which may comprise, for example, filtration, separation, dilution, pasteurization and carbonation systems.

The inventive method can also include the further step of selectively applying anolyte, preferably having a pH (undiluted) in the range of from about 6.0 to about 6.5, an ORP (undiluted) of ≧+950 mV and a Free Available Oxidant concentration (undiluted) of ≦300 ppm, so as to continuously neutralize residual microbial contaminants, as well as to effect a residual disinfection of downstream process equipment for control of potentially recontaminating biofilm growth. The anolyte will preferably be introduced into the general process water at a concentration of up to 20 parts by volume anolyte per 80 parts by volume water. This step preferably involves low dose inclusion of anolyte, on a continuous basis, into the general process water stream so as to eliminate newly introduced microbes from the water supply system (municipal authority, borehole, etc.) and to also manipulate the charge of the treated water to prevent the further or new growth of biofilm which might otherwise result from irregular interventions of anolyte treatment during the CIP process or elsewhere. The continuous low dose anolyte application serves to both eliminate new microbes introduced into the system and to prevent the new growth of biofilm which would create a new source of microbial contamination over time. The points of application in the overall process flow will preferably correspond with the targeted microbe to biocide contact period as described by the minimum dwell time within the process, itself correlated with the magnitude of anolyte dilution and the minimum levels of microbial decontamination required within the treated process water. Typically large batch production volumes will require extended processing time and thus protracted storage and packaging periods.

In accordance with the present invention, examples of points or systems in typical beverage production processing and packaging units where catholyte, either in concentrated or preferably in aqueous diluted form, can be introduced as a cleaning solution include, but are not limited to: (a) water treatment areas for, e.g., mixing with flocculation and floor washing; (b) ultra filtration module areas for, e.g., membrane cleaning, downstream and upstream disinfection and sterilizing, and as a replacement for detergents and other agents in the Clean-in-Place (CIP) system; (c) soil removal; and (d) chain lube biofilm removal for product decontamination.

When used for cleaning the interiors of fermentation vessels in breweries, the catholyte cleaning solution will preferably comprise (a) an electrochemically-activated water catholyte solution and (b) an amount of a food grade non-ionic surfactant effective to reduce, and most preferably to prevent, foam formation in the fermentation vessel. Without the surfactant, oily organic residues in the fermentation vessel will cause the formation of a foam which will greatly inhibit the physical shearing action of the catholyte solution, thus significantly reducing its cleaning effectiveness. However, I have discovered that the addition of a relatively small amount of non-ionic surfactant to the cleaning composition is effective for reducing or preventing foam formation, thereby greatly enhancing the cleaning effectiveness of the catholyte solution.

The electrochemically-activated water catholyte solution used in the fermentation vessel cleaning composition can be in undiluted or in aqueous dilution form and will preferably comprise a catholyte product which, when in undiluted form, has a negative oxidation-reduction potential of at least −110 mV and a pH in the range of from about 8 to about 13. The catholyte solution will preferably be an aqueous dilution of the catholyte product comprising at least 50% by volume (more preferably at least 70% and most preferably at least 80% by volume) of nonelectrolyzed water based on the total combined volume of the nonelectrolyzed dilution water and the catholyte product.

Examples of non-ionic surfactants suitable for use in the fermentation vessel cleaning composition include, but are not limited to, Biosil AF 720F, which is an aqueous emulsion comprising polysiloxane, treated silica, and an emulsifier, and polyoxyethylene surfactants. The non-ionic surfactant will preferably be used in an amount of at least 10 mg per liter of the catholyte cleaning composition (or 10 ppm). Higher amounts of the surfactant will typically be preferred as the concentration of the catholyte solution increases.

Examples of areas in a typical beverage production processing and packaging plant where anolyte, either in concentrated or preferably in aqueous diluted form, can be used as a disinfecting wash or agent include, but are not limited: (a) water treatment applications including, e.g., replacing chlorine disinfectants and biofilm removal; (b) ultra filtration module area applications including, e.g., membrane cleaning, downstream and upstream disinfection and sterilization, and as a replacement for CIP chemical agents and washes heretofore used in the art; (c) biofilm removal, biofilm control and sugar removal; (d) product decontamination applications including, e.g., chain lube biofilm removal, replacement of CIP chemicals heretofore used in the art, and nozzle cleaning; and (e) bottle washing applications including bottle and cap cleaning.

Figure 4A:
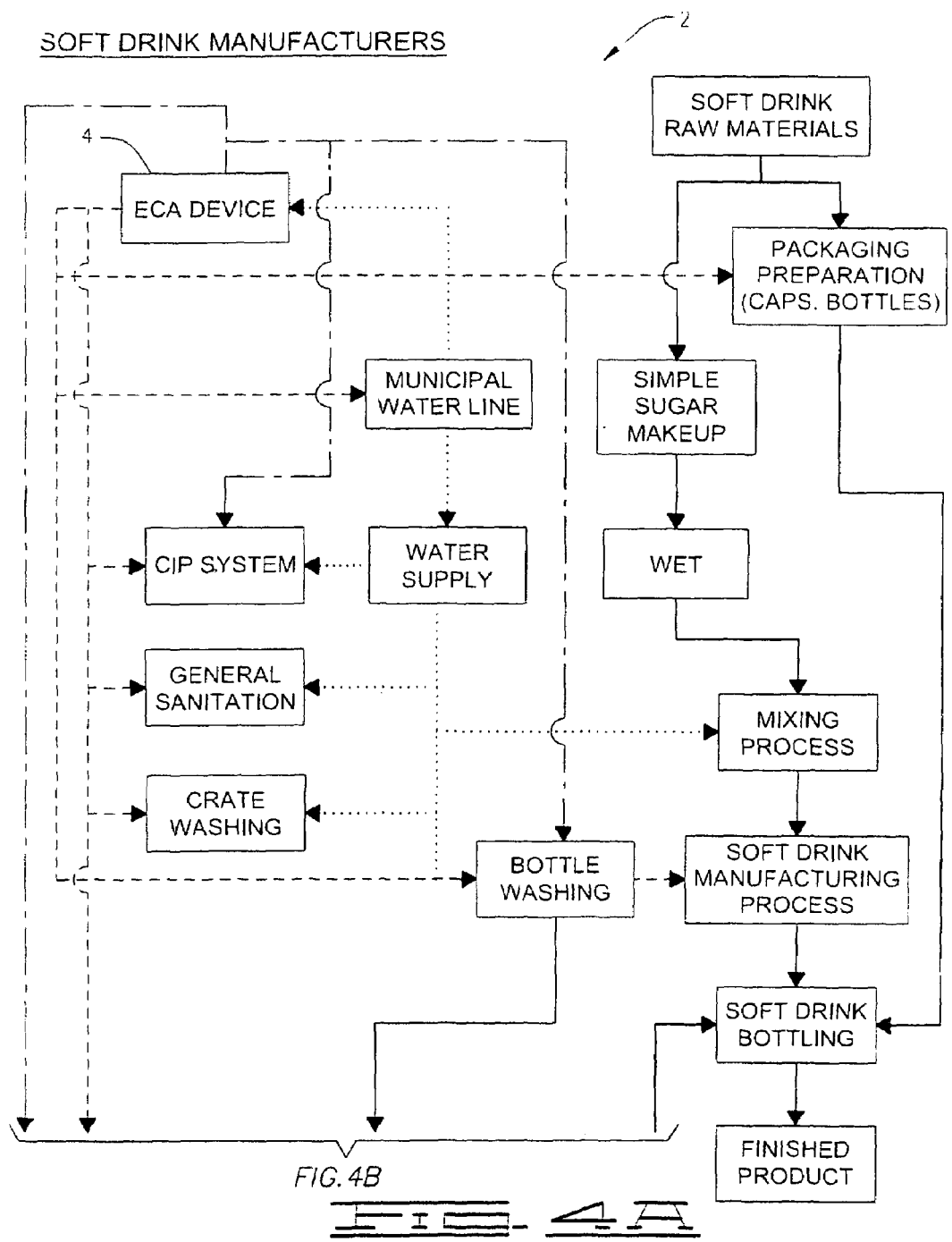
FIG. 4 is a flow diagram illustrating an embodiment 2 of an improved soft drink production, processing, and packaging system provided by the present invention.
Figures 4A, 4B:
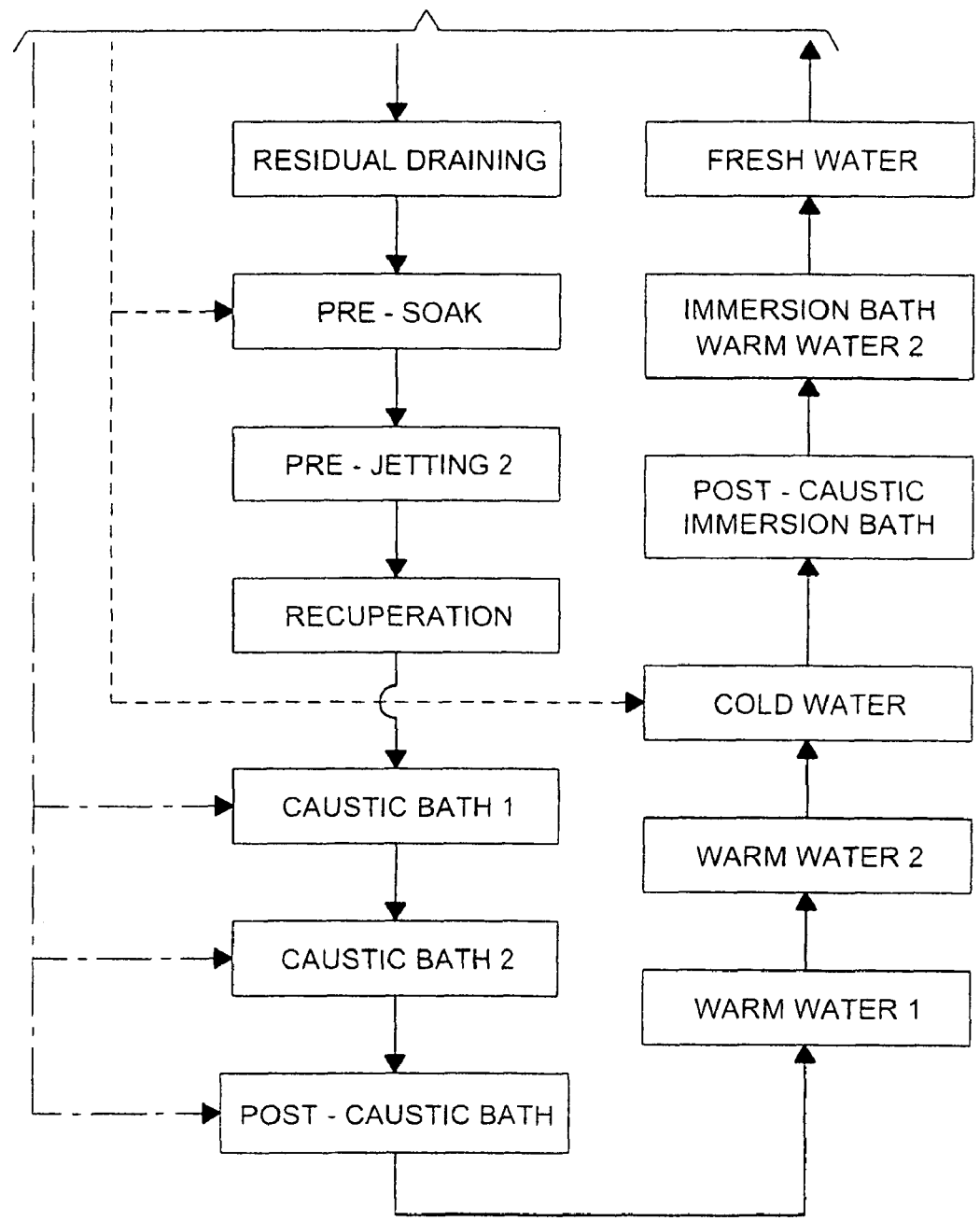

FIG. 4 schematically illustrates a soft drink production processing and packaging system 2 which has been improved to utilize ECAW at various points and in various subsystems. The soft drink line 2 includes an electrochemical activation system/reactor unit 4 for producing an anolyte and a catholyte product. Examples of systems, subsystems and points wherein concentrated or aqueous diluted catholyte washing solutions are introduced and used in the soft drink production line 2 include: bottle washing; bottle washing caustic bath applications; and in the Clean-in-Place (CIP) system for substantially the entire the line 2 or any portion thereof. Examples of systems, subsystems and points wherein concentrated or aqueous diluted anolyte disinfecting wash solutions are introduced and used in accordance with the present invention include: the CIP system for substantially the entire line 2 or any portion thereof; water treatment; general sanitation; crate washing; bottle soaking and washing; cap and bottle preparation; and as a beverage ingredient.

Figure 5A:
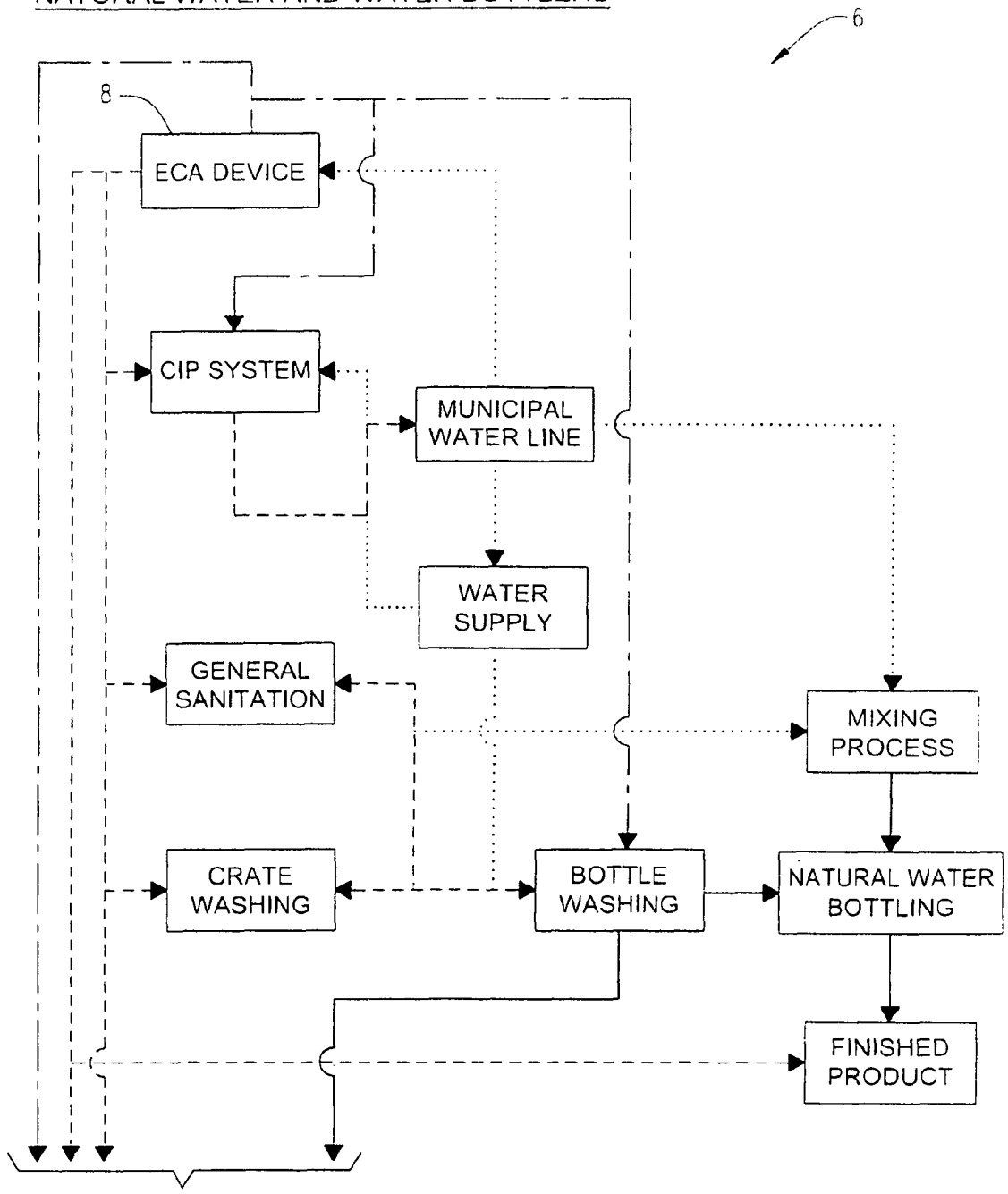
FIG. 5 is a flow diagram illustrating an embodiment 6 of an improved bottled water production system provided by the present invention.
Figure 5A:
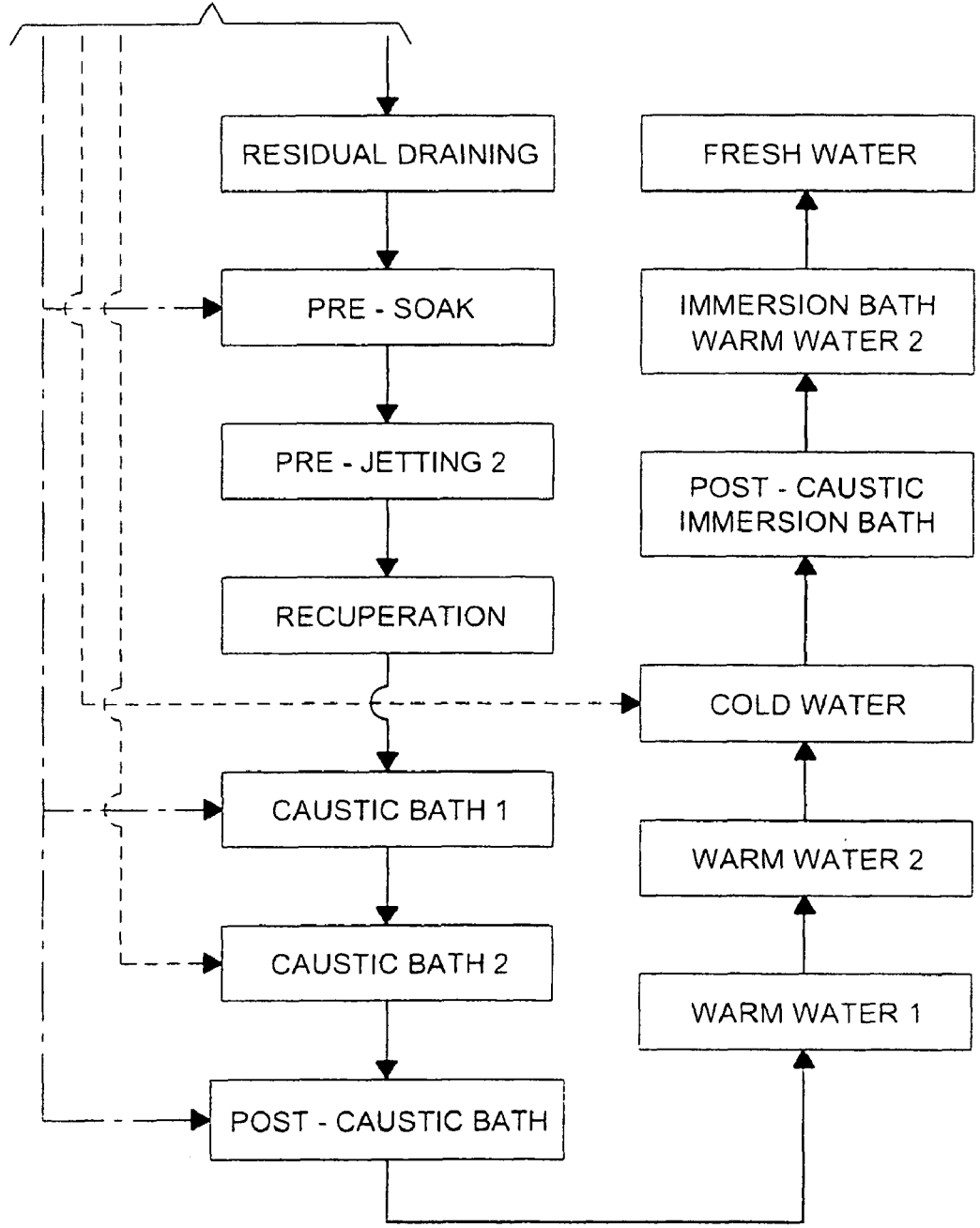

FIG. 5 schematically illustrates an improved bottled water processing and packaging system 6 which utilizes anolyte and catholyte treatments in accordance with the present invention. The improved bottled water line 6 includes an electro-chemical activation system/reactor 8 for generating the anolyte and catholyte materials used. Examples of systems, subsystems and points within the bottled water line 6 wherein concentrated catholyte or aqueous diluted catholyte washing solutions are used include: the CIP system; bottle washing; and bottle washing caustic bath and soaking operations. Examples of systems, subsystems and points wherein concentrated anolyte or aqueous diluted anolyte disinfecting wash solutions are used include: the CIP system; water treatment; general sanitation; crate washing; bottle washing; caustic bath applications; and finished product.

FIG. 6 illustrates an improved fruit juice production, processing, and bottling system 10 wherein ECWA solutions are used in accordance with the present invention. The fruit juice line 10 includes an electrochemical activation system/reactor 12 which produces anolyte and catholyte materials used in the inventive process. Examples of systems, subsystems and points wherein concentrated catholyte or aqueous diluted catholyte wash solutions are used in the fruit juice line 10 include the CIP system, bottle washing, and mixing. Examples of systems, subsystems and points wherein concentrated or aqueous diluted anolyte disinfecting solutions are used in accordance with the inventive process include: the CIP system; general sanitation; crate washing; bottle washing; water treatment; and as a product ingredient.

FIG. 7 schematically illustrates an improved wine production and bottling system 14 wherein ECAW is used in accordance with the present invention for several purposes. The improved wine production and bottling line 14 includes an electrochemical activation system/reactor 16 for producing the anolyte and catholyte materials used in the improved process. In the improved wine production and bottling line 14, examples of systems, subsystems, and points wherein concentrated catholyte or aqueous diluted catholyte washing solutions are used include the CIP system, bottle washing, manufacturing, and bottling. Examples of systems, subsystems and points wherein concentrated anolyte or aqueous diluted anolyte sanitizing solutions are used in the wine production and bottling line 14 include: the CIP system; water treatment; general sanitation; crate washing; and bottle washing.

FIG. 8 schematically illustrates an improved beer production and bottling system 18 wherein ECAW is used in accordance with the present invention for various purposes. The improved beer production and bottling line 18 includes an electrochemical activation system/reactor 20 for generating the anolyte and catholyte materials used in the improved system. Examples of systems, subsystems and points wherein concentrated catholyte or aqueous diluted catholyte wash solutions are employed in the improved beer production and bottling line 18 include the CIP system, bottle washing, manufacturing, and bottling. Examples of systems, subsystems and points wherein concentrated anolyte or aqueous diluted anolyte disinfecting solutions are employed in the improved beer processing and bottling line 18 include: the CIP system; general sanitation; water treatment; crate washing; bottle washing; and as a beer ingredient.

The inventive method also includes the use of electrochemically activated aqueous anolyte as a disinfectant remedy against general microbial and specific biofilm contamination of the charcoal granules in a GAC filtration system. The REDOX potential of the anolyte solution at various dilutions is employed to manipulate the surface charge and hence the free energy of the charcoal granules, which supports the microbial and biofilm presence. This intervention comprises the step of contacting the granular charcoal material with an anolyte solution having a pH (undiluted) in the range of from about 4.5 to about 7.5 and an ORP (undiluted) in the range of from about +650 mV to $\geq$+900 mV, preferably by introducing the anolyte into the process water used in flushing the GAC system.

The invention further includes an electrochemically activated aqueous anolyte product with a pH (undiluted) in the range of from about 4.5 to about 7.5 and an ORP (undiluted) in the range of from about +650 mV to $\geq$+900 mV for use, preferably in aqueous diluted form, as a treatment agent for the process water used in the disinfection of the systems and equipment used in the production, processing, and packaging of diverse beverage products.

The invention also extends to the use of electrochemically activated aqueous anolyte as an oxidant in the elimination of contaminating chemical residues, including dedicated product flavors and ingredients encountered, for example, when switching a beverage system from the production of one beverage product to another. This step comprises contacting the system and equipment components with an anolyte having a pH (undiluted) in the range of from about 4.5 to about 7.5, an ORP (undiluted) in the range of from about +650 mV to $\geq$+900 mV and a Free Available Oxidant concentration (undiluted) of <300 ppm. The anolyte is preferably applied in aqueous diluted form.

The invention further includes an electrochemically activated aqueous anolyte with a pH (undiluted) in the range of from about 4.5 to about 7.5, an ORP (undiluted) in the range of from about +650 mV to $\geq$+900 mV, and a Free Available Oxidant concentration (undiluted) of $\leq$300 ppm, for use as an oxidant in the treatment of process water to eliminate pesticide and fungicide residues.

The invention also includes an electrochemically activated aqueous anolyte with a pH (undiluted) in the range of from about 4.5 to about 7.5, an ORP (undiluted) in the range of from about +650 mV to $\geq$+900 mV, and a Free Available Oxidant concentration (undiluted) of $\leq$300 ppm, for use as a treatment agent for the decontamination of the pore surfaces of carbon granules, as well as for the neutralization of pesticide residues, in Granular Activated Charcoal columns.

The following is an example of a preferred procedure for the treatment of granular activated charcoal (GAC) columns with electrochemically activated water (ECAW) solutions. This procedure is described as related to standard filtration systems using GAC. The application protocol can be readily adapted to accommodate differences in the design of the filtration vessels and/or the flow dynamics of the filtrate.

The inventive process desirably uses the unique attributes of the energized ECAW solutions to disrupt the surface free energy and thus the intrinsic charge environment of the GAC granules, and further uses this manipulation of charge to effect a release of electrostatically bound biofilm soils and organic debris from the charcoal surface, as well as to scavenge labile energy from the system as a dedicated biocidal intervention.

This is reliably and effectively achieved by the sequential application of ECAW catholyte and anolyte solutions. The mobilization and removal of the established organic soiling and biofilm growth by the introduction of the "energy-rich" catholyte solution is facilitated by the catholyte's latent detergent and de-agglomerative reducing properties. Similarly, the neutralization of the free floating and granule-adherent microbes within the GAC bed is achieved by the presence of the high oxidant anolyte solution.

In terms of evaluating the performance of the two ECAW solutions, the measurement of the physio-chemical properties of the solutions before and after delivery through the GAC vessel can be used to calculate the degree of intervention achieved. However, it will be appreciated that the charge on the GAC granules will be altered in a progressive and cumulative manner, and that a gradient of altered charge through the depth of the column will develop as a result of contact with the ECAW solutions. Thus, the granules in contact with the 'fresh' solution at the point of application will display the greatest alteration in charge with the effect being progressively diluted as the ECAW solutions percolate through the GAC bed. This charge 'sacrifice' is a result of the energy demand placed on the applied filtrate solution by the surface free energy of the granules, and requires either continuous flow or repetitive applications of the ECAW solutions to progressively increase the degree of charge alteration to the granules at increasing depths within the GAC column.

Thus, the less difference that is observed between the measured properties of the ECAW influent and effluent solutions, the greater the degree of efficacy that will have been achieved. Catholyte solutions should thus be maintained effectively reducing throughout the GAC bed while the anolyte solutions should be maintained at a high oxidant state.

Figure 9:
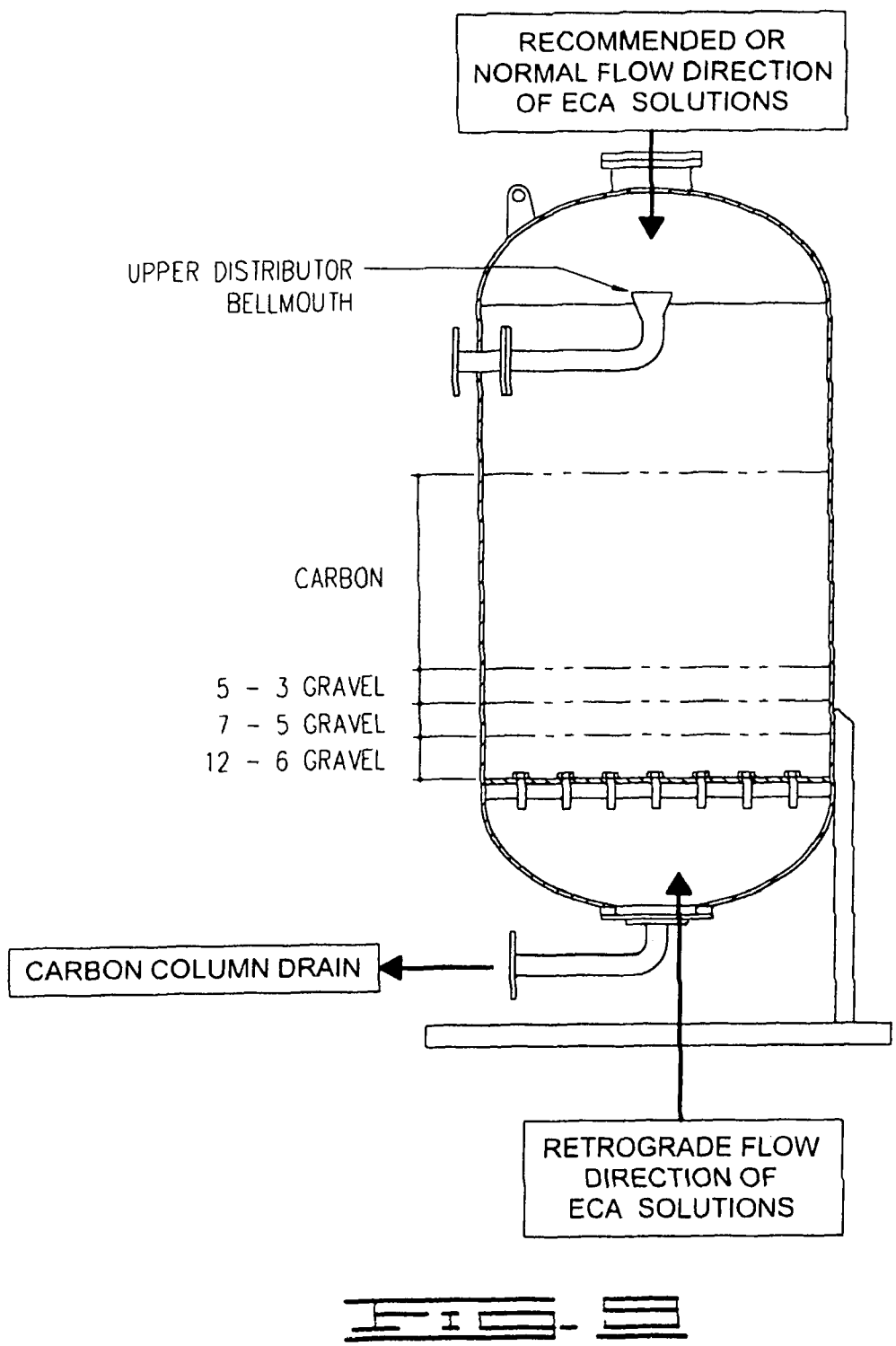
FIG. 9 schematically illustrates a method provided by the present invention for treating granular activated carbon (GAC) filtration systems.

For purposes of illustration, the procedure provided by the present invention is now described using the standard vessel design shown in FIG. 9.

In order to optimize the integrity of the physio-chemical measurements used to predict the performance of the different ECAW solutions, the baseline values of these same properties for the water stream in the GAC column prior to introducing any ECAW solutions are preferably first measured. The same sets of measurements for both the influent and effluent water stream are captured to determine the current performance of the GAC granules in terms of influencing filtrate water quality, as well as to serve as a base-line for comparison with the effects of the intervention with the ECAW solutions.

The data is interpreted in terms of the age of the granules in the column and the current practices with regard to disinfection and charge regeneration/rehabilitation, as well as the design and flow dynamics of the filtration vessel.

These measurements preferably comprise the following:
Oxidation reduction potential (ORP)—milliVolts (mV)
Electrical Conductivity (EC)—milliSiemens/centimeter (mS/cm)
Free Active Oxidants (FAO)—parts per million/milligram/liter (ppm/mg/lit)

Typically, the solutions used in the inventive GAC treatment will preferably be of the following measured values and minimum volumes:

| Solution | ORP (mV) | pH | EC (mS/cm) | Volume (lit) |
| --- | --- | --- | --- | --- |
| Anolyte | $\geq +900$ | ±6.5-7.0 | ±5.5-6.0 | 3000 |
| Catholyte | $\leq -900$ | ±11.0 | ±5.5-6.0 | 3000 |

The preferred procedure for treating the GAC column illustrated in FIG. 9 with ECAW solutions is as follow:
1. Drain all possible residual water out of the GAC vessel.
2. Fresh solutions of Anolyte and Catholyte are preferably generated on-site in sufficient quantities to permit a continuous treatment to be undertaken.
3. Measure the ORP, pH and EC of the Catholyte at the inlet treatment point of the vessel.
4. Fill the GAC vessel with concentrated Catholyte solution in a normograde flow direction and allow the catholyte solution to fill above the level of the carbon bed.
5. The Catholyte solution can be dosed in through the port at the top of the vessel or through the existing inlet pipe which connects to the upper distribution bellmouth. This will typically require 5-20 minutes.
6. Allow the Catholyte solution to drain freely through the bottom drain port or valve. This will typically take 5-10 minutes.
7. Measure the ORP, pH and EC of the effluent Catholyte solution at the outlet point of the vessel.
8. Repeat the dosing of the Catholyte solution in a retrograde flow direction (i.e. from the bottom upwards) after measuring the ORP, pH and EC of the solution.
9. Allow the Catholyte solution to drain freely and measure the ORP, pH and EC of the effluent solution.
10. Repeat the dosing and measurements as detailed in steps 8 and 9.
11. Repeat the normograde dosing of Catholyte in accordance with the procedures detailed in steps 5-7.
12. While two repeated applications of the Catholyte solution will typically be adequate to mobilize biofilm aggregations, the number of repetitions of the dosing schedule may be increased, and this will be governed by the degree of biofilm growth, organic soiling or microbial bioload.
13. The vessel will preferably be drained completely of all possible residual Catholyte effluent.

Anolyte Dosing
14. Measure the ORP, pH and EC of the Anolyte at the inlet treatment point of the vessel.
15. Fill the GAC vessel with concentrated Anolyte solution in a normograde flow direction and allow the Anolyte solution to fill above the level of the carbon bed.
16. The Anolyte solution can be dosed in through the port at the top of the vessel or through the existing inlet pipe which connects to the upper distribution bellmouth. This will typically take 5-20 minutes.
17. Allow the Anolyte solution to drain freely through the bottom drain port or valve. This will typically take 5-10 minutes.
18. Measure the ORP, pH and EC of the effluent Anolyte solution at the outlet point of the vessel.
19. Repeat the dosing of the Anolyte solution in a retrograde flow direction (i.e. from the bottom upwards) after measuring the ORP, pH and EC of the solution.

20. Allow Anolyte solution to drain freely and measure the ORP, pH and EC of the effluent solution.
21. Repeat the dosing and measurements as detailed in steps 19 and 20.
22. Repeat the normograde dosing of Anolyte in accordance with the procedures detailed in steps 16-18.
23. Drain all residual Anolyte effluent from the system and introduce softened treated water to flush residual ECAW solutions from the GAC filtration system. This will have been accomplished when parity is achieved between the physio-chemical properties of the influent water and the effluent water streams.

In addition to rehabilitating the charge of and to disinfecting the activated carbon granules, the use of ECAW solutions used in accordance with the inventive method further operates to neutralize pesticide residues and build-up in the GAC system.

Without limiting the scope thereof, the invention will now be further described and exemplified with reference to the following examples and experimental results.

EXAMPLE 1

This was a comparative test involving the use of ECAW solutions to replace the existing chemical agents used in conventional Cleaning-in-Place (CIP) protocols. As shown below, the inventive method provided enhanced microbial control, reduced water usage, and shorter cleaning and disinfection cycles in a carbonated beverage plant.

Conventional cleaning and disinfection of systems and equipment in carbonated beverage packaging plants has typically comprised two protocols—either a three step (only disinfection) or a five step process (cleaning, rinsing and disinfection).

Antioxidant catholyte and oxidant anolyte were added to process water used for the cleaning and disinfection of production and packaging systems and equipment for diverse beverage types as a complete substitution for existing conventional chemical products. The measured characteristics of the diluted aqueous treatment solutions used were as follows:

| Solution*     | EC** | pH   | ORP | FAO |
|---------------|------|------|-----|-----|
| 5% Anolyte    | 0.67 | 6.6  | 740 | <25 |
| 30% Catholyte | 2.72 | 10.8 | 220 | 0   |
| 30% Anolyte   | 2.0  | 6.8  | 890 | 80  |

*Solution concentrations expressed as vol %.
**Electrical conductivity (mS/cm—milliSiemens per centimeter)

A comparative trial was conducted in a representative carbonated beverage manufacturing and packaging plant. The conventional cleaning chemicals used in the comparative trial comprised a 2-3% chlor-alkaline caustic soda (NaOH) solution employed at ambient temperature. The conventional disinfectant solution comprised either a sodium or calcium hypochlorite solution or equivalent oxidant agent dosed at ambient temperature into the system at a rate of 50 ppm of Free Available Chlorine (FAC) content. The protocols for the conventional procedure were as follows:

TABLE 1

CIP protocols using conventional chemicals

| Process Step | 5 Step | 3 Step |
|---|---|---|
| Initial Rinse with treated water | 5 to 10 minutes<br>±7000 l treated water used | 5 to 10 minutes<br>±7000 l treated water used |
| Detergent Cleaning | 15 to 20 minutes @ 2.5% chloralkali<br>±10000 l treated water used | Excludes time for manual CIP changeover - Est. 20 minutes |
| Treated water rinse | 5 to 10 minutes<br>±7000 l treated water used | 5 to 10 minutes<br>±7000 l treated water used |
| Sanitation | 20 to 30 minutes @ 50 mg/l<br>±10000 l treated water used | 20 minutes @ 50 mg/l<br>±10000 l treated water used |
| Treated water Rinse | 5 to 10 minutes<br>±7000 l treated water used | 5 to 10 minutes<br>±7000 l treated water used |
| TOTAL TIME | 50-80 minutes | 35 to 50 minutes |
| Total Solution Usage | ±41,000 l CIP solution used | ±31,000 l treated water used |

For purposes of comparison, the following protocols were then initiated using the ECAW solutions in accordance with the inventive method:

TABLE 2

CIP protocols using the ECA solutions

| Process Step | 5 Step | 3 Step |
|---|---|---|
| Initial Rinse with 5% Anolyte treated water | <10 minutes<br>±3000 l treated water used | <10 minutes<br>±3000 l treated water used |
| Detergent Cleaning | 15 minutes @ 30% Catholyte<br>±3000 l treated water used | Nil |
| Treated water rinse | Nil | Nil |
| Sanitation | 15 minutes @ 30% Anolyte<br>±3000 l treated water used | 15 minutes @ 30% Anolyte<br>±3000 l treated water used |
| Treated water Rinse | <10 minutes<br>±3000 l treated water used | <10 minutes<br>±3000 l treated water used |
| TOTAL TIME | 50 minutes | 35 minutes |
| Total Solution Usage | ±12,000 l CIP solution used | ±9,000 l treated water used |

Figure 2:
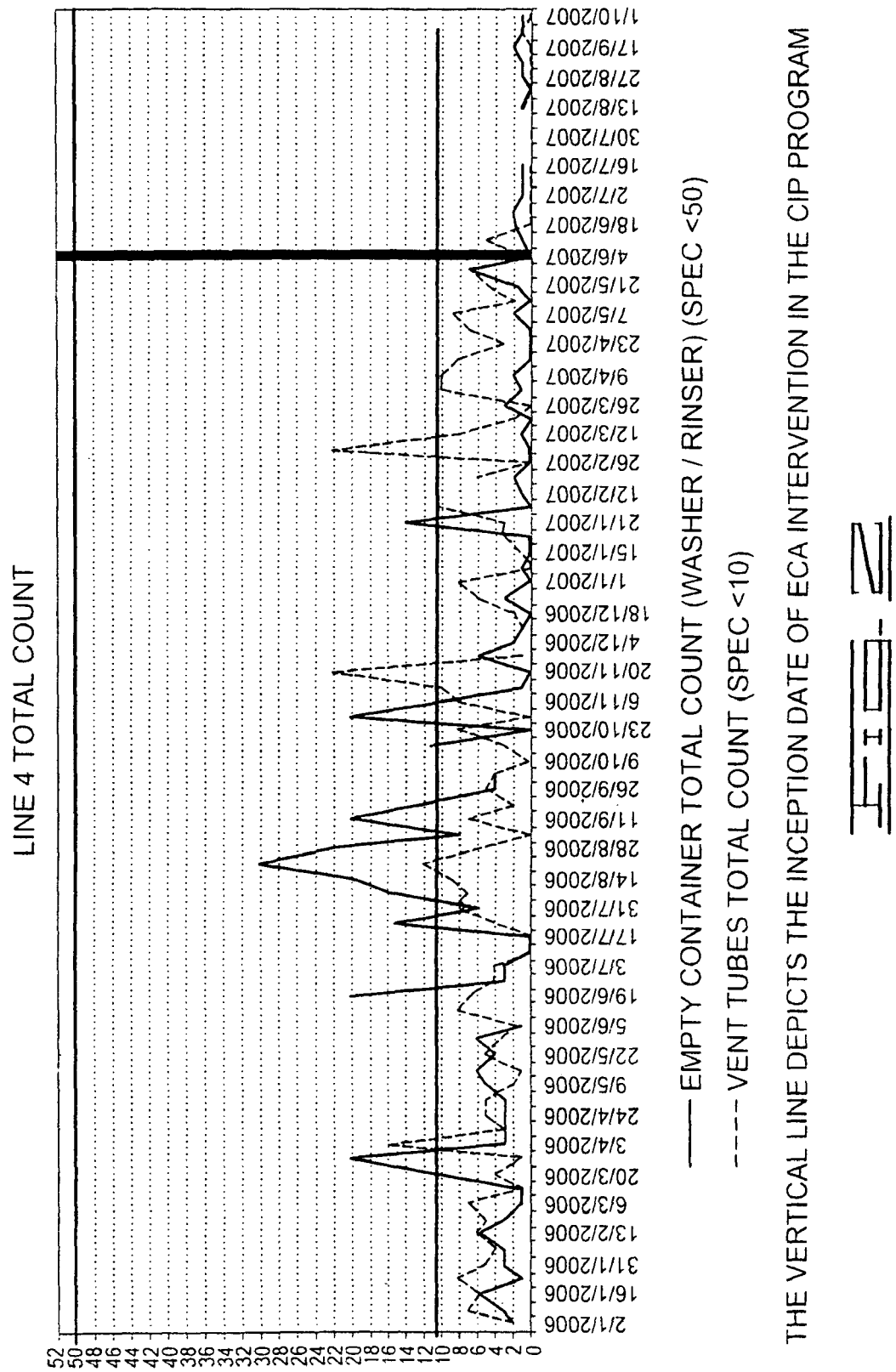
FIG. 2 is a chart showing microbial count results obtained in Example 1 in filling equipment and containers.
Figure 11:
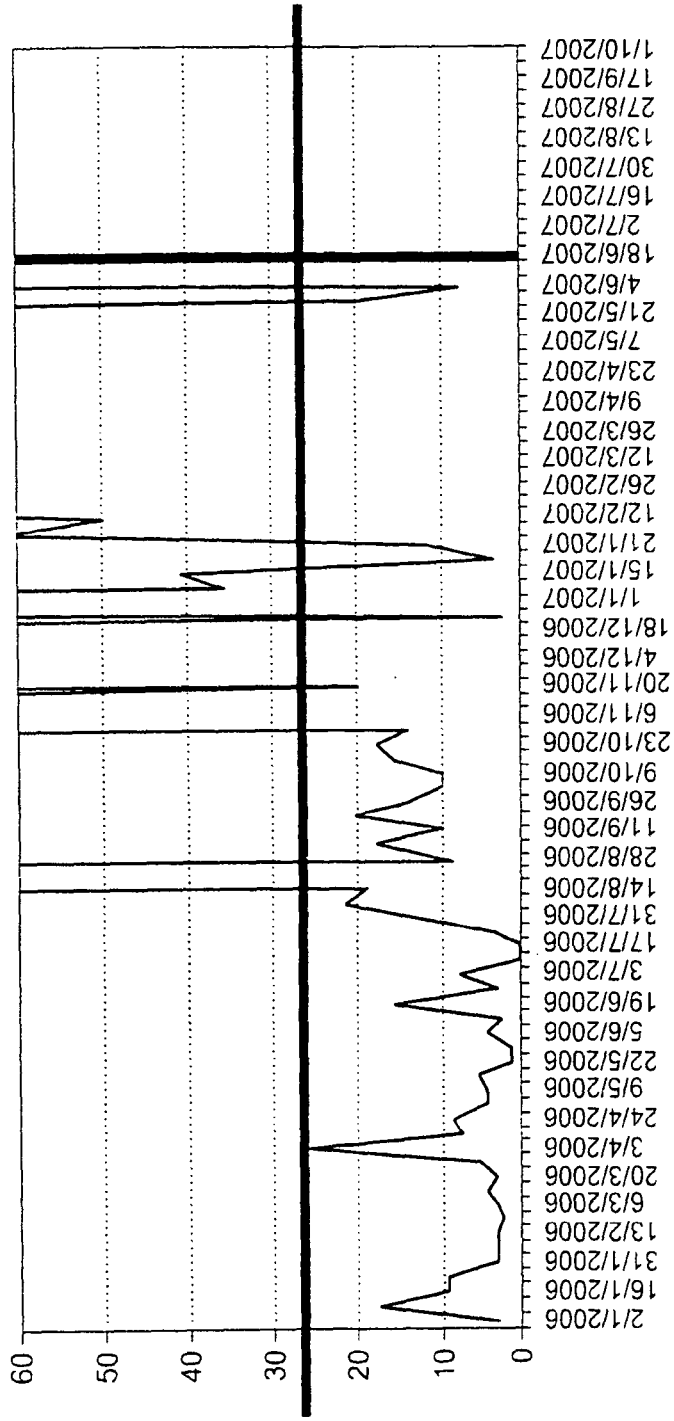

The antimicrobial efficacy of the oxidant anolyte solution is reflected in FIGS. 1, 2 & 3.

A standard membrane filtration method was used to test all microbiological samples. Swabs were collected as per recognized standard protocols.

Conclusions:

Aside from the complete elimination of conventional cleaning and disinfecting chemicals, the integration of the ECA solutions into both the 3 and 5 step CIP procedures resulted in a significant reduction in water usage and a substantial saving in the time required to complete the CIP process.

EXAMPLE 2

Carbonation of ECA Solutions

Carbonation of predetermined, diluted ECA solutions was conducted to establish the changes in the physiochemical characteristics that resulted from the addition and presence of gaseous Carbon Dioxide ($CO_2$).

Standard dilutions of freshly generated ECA anolyte and catholyte were prepared using untreated potable process water. The physiochemical attributes of each solution were recorded both before and after carbonation in order to detail the changes effected by the introduction of $CO_2$.

As will be understood by those in the art, the various solutions tested in this example were carbonated by the application of 2.5 volumes (5 gm/500 ml) of $CO_2$ to 500 ml of the sample at ambient temperature for 30 seconds.

TABLE 3

Physiochemical parameters of the ECA solutions before and after carbonation.

| Parameter | Catholyte @ 30% | | Concentrate Catholyte |
|---|---|---|---|
| | Before | After | |
| EC (mS) | 3.38 | 2.53 | 9.93 |
| pH | 11.3 | 5.4 | 11.6 |
| ORP (mV) | 15 | 441 | −110 |

| Parameter | Anolyte @ 30% | | Concentrate Anolyte |
|---|---|---|---|
| | Before | After | |
| EC (mS) | 2.8 | 2.63 | 8.14 |
| pH | 6.9 | 4.7 | 7.0 |
| ORP (mV) | 830 | 980 | 885 |
| FAO (ppm) | 80 | 80 | +200 |

| Parameter | Anolyte @ 5% | |
|---|---|---|
| | Before | After |
| EC (mS) | 0.69 | 0.6 |
| pH | 6.9 | 4.7 |
| ORP (mV) | 823 | 930 |
| FAO (ppm) | 20-25 | 20-25 |

Legend:
ORP—Oxidation-Reduction Potential (mV—milliVolt),
EC—Electrical Conductivity - (mS/cm—milliSiemens per centimeter),
FAO—Free Available Oxidants (ppm—parts per million)

In terms of the Catholyte solution, there was a substantial shift in REDOX potential from a substantially reducing capability to being a weak oxidant.

It has been repeatedly demonstrated that ORP is a reliable measure of potential antimicrobial efficacy of anolyte solutions at different dilution rates and that, with a prior knowledge of the extent of microbial bioload (cfu/ml) in a system, the anolyte solution required to eliminate microbial contamination can be accurately titrated on the basis of this relationship. The addition of $CO_2$ to the diluted anolyte solutions resulted in a surprising and substantial upwards shift in REDOX potential with an increased oxidant activity and was paralleled by an equivalent reduction in pH which also serves to potentiate the biocidal activity of the ECA disinfectant solutions.

Conclusion:

The carbonation of ECA solutions results in substantial shifts in the physicochemical parameters affecting cleaning and microbicidal capacity. The elevated REDOX potential of the carbonated anolyte provides an enhanced antimicrobial capability relative to non-carbonated anolyte.

EXAMPLE 3

Residue Neutralization

The breakdown of pesticide and fungicide residues by an oxidant ECA anolyte solution was evaluated as follows.

The oxidant anolyte solution was diluted using a 10 fold dilution series. As a control for this test, the potential for non-ECA based hydrolysis or chemical breakdown was assessed using two untreated control solutions, one being the tap water used as the diluent in the anolyte dilution series and the other being the non-activated brine solution that was used as the electrolysis feed solution prior to electro-activation.

The experiment was performed to contrast the difference in degree of recovery of a variety of pesticide and fungicide active ingredients (AI's) after the tap water and the various diluted anolyte solutions were 'spiked' with the same AI's at fixed inclusion rates. In each case, a one ppm cocktail of the active ingredients was added to a 100 ml aliquot of the test or control solution sample. The test samples were agitated with a mechanical stirrer for 5 minutes at ambient temperature and then extracted with an organic solvent and analyzed by either gas or liquid chromatography.

TABLE 4

Physiochemical parameters of the control and anolyte test solutions

| Solution type | ORP (mV) | pH | EC (mS/cm) | FAO (ppm) |
|---|---|---|---|---|
| Tap water control | 280 | 8.2 | 0.21 | — |
| 2.5 gm/lit salt solution nonactivated | 290 | 7.7 | 5.22 | — |
| 1% Anolyte solution | 436 | 7.5 | 0.35 | ≦5 |
| 10% Anolyte solution | 803 | 7.2 | 1.34 | 20-25 |
| 100% Anolyte solution | 940 | 6.5 | 5.45 | ≦200 |

Legend:
ORP—Oxidation-Reduction Potential (mV—milliVolts),
EC—Electrical Conductivity (mS/cm—milliSiemens per centimeter),
FAO—Free Available Oxidant concentration (ppm—parts per million).

TABLE 5

Mass and percentage recovery and breakdown of a range of pesticide and fungicide Active Ingredients (AI's) after exposure to a variety of anolyte dilutions.

| Active Ingredient | Chemical type | Tap water (ng) | 0.25% Brine | | 1% Anolyte solution | | | 10% anolyte solution | | | 100% anolyte solution | | |
|---|---|---|---|---|---|---|---|---|---|---|---|---|---|
| | | | ng found | % recovery | ng found | % recovery | % break-down | ng found | % recovery | % break-down | ng found | % recovery | % break-down |
| Malathion | Organophosphorus insecticide | 0.066 | 1,327 | 126.1 | 1.368 | 130.2 | 0.0 | 0.066 | 0.0 | 100 | 0.067 | 0.1 | 100 |
| Chlorpyrifos | Organophosphorus insecticide | 0.05 | 1.014 | 96.4 | 1.039 | 98.9 | 0.0 | 0.05 | 0.0 | 100 | 0.049 | −0.1 | 100 |
| Cyprodinil | Anilino-pyrimidine fungicide | 0.031 | 1.297 | 126.6 | 1.356 | 132.5 | 0.0 | 0.068 | 3.7 | 96.3 | 0.026 | −0.5 | 100 |
| Kresoxim-methyl | Strobilurin fungicide | 0.029 | 1.300 | 127.1 | 1.328 | 129.9 | 0.0 | 1.344 | 131.5 | 0.0 | 0.035 | 0.6 | 100 |
| Bupirimate | Pyrimidine Fungicide | 0.052 | 1.250 | 119.8 | 1.233 | 118.1 | 0.0 | 0.730 | 67.8 | 52.0 | 0.074 | 2.2 | 100 |
| Azinphos-methyl | Organophosphorus insecticide | 0.095 | 2.341 | 224.6 | 2.393 | 229.8 | 0.0 | 0.000 | −9.5 | 100 | 0.000 | −9.5 | 100 |
| Benomyl | Benzimadazole fungicide | 0.000 | 0.970 | 97.0 | 0.890 | 89.0 | 8.0 | 0.520 | 52.0 | 45 | 0.000 | 0.0 | 100 |
| Aldicarb | Carbamate insecticide | 0.000 | 0.920 | 92.0 | 0.425 | 42.5 | 49.5 | 0.000 | 0.0 | 100 | 0.000 | 0.0 | 100 |
| Aldicarb sulfoxide | Carbamate insecticide | 0.000 | 0.672 | 67.2 | 0.514 | 51.4 | 15.8 | 0.000 | 0.0 | 100 | 0.000 | 0.0 | 100 |
| Methomyl | Carbamate insecticide | 0.000 | 1.006 | 100.6 | 0.634 | 63.4 | 36.6 | 0.000 | 0.0 | 100 | 0.000 | 0.0 | 100 |

Legend:
ng—nanograms

Conclusion

The organophosphorus and carbamate group pesticides and the benzimidazole, anilinopyrimidine, strobilurin, pyrimidine, and benzimidazole based fungicides were all oxidized by exposure to the anolyte solutions.

EXAMPLE 4

Microbial Decontamination and Surface Free Energy Manipulation of Activated Charcoal Granules with ECA Solutions ECA solutions were applied to a standard Granular Activated Charcoal (GAC) column vessel with an active filtration bed dimension of 2000 mm depth and 1700 mm diameter. Commercial (F200 grade) activated charcoal granules with a bulk density of 500 kg/m$^3$ were overlaid above with a graduated pebble bed of varying sizes and densities. The charcoal granule bed had become progressively contaminated with a mature microbial biofilm and optimal operational rehabilitation of the granules using conventional procedures would have required either extended steam pasteurization or complete replacement of the granules.

In light of the specific adsorption characteristics of the charcoal granules based on surface free energy, an antioxidant catholyte was initially used to manipulate the surface tension of the filtrate water at the biofilm:charcoal granule interface promoting the disruption of the adsorbed inorganic biofilm matrix. The changes in the physiochemical attributes of the influent solutions were contrasted against those of the effluent stream and these differences described the degree of surface free energy manipulation achieved as well as served to predict the degree of alteration of adsorptive capacity at the charcoal granule surface.

Following continuous catholyte infusion, steeping and drainage, an anolyte solution was introduced and the physiochemical characteristics of both the influent and effluent streams were contrasted to detail when the optimum Oxidation Reduction Potential had been attained within the bed in order to achieve the required antimicrobial effect.

Optimal admixture of the ECA solutions with the surfaces of the charcoal granules was achieved by introducing the ECA solutions from both the top as well as the bottom of the filter vessel and this protocol increased granule surface exposure by disrupting the channeling of filtrate through existing flow configurations in the granule bed.

TABLE 6

Changes in the physiochemical attributes of the ECA solutions applied to a GAC vessel over time
Changes in physiochemical parameters of Catholyte and Anolyte solutions when introduced into a Granular Activated Charcoal column over time

| Time | Solution type | Activity | ORP | pH | EC | Δ ORP Feed-Effluent |
|---|---|---|---|---|---|---|
| | Anolyte | Pretreatment | 935 | 6.6 | 5.15 | |
| | Catholyte | Pretreatment | −804 | 11.1 | 6.61 | |
| 09:10 | Catholyte | Pump Top | −804 | 11.1 | 6.61 | |
| 09:20 | Catholyte | drain | 65 | 9.8 | 5.15 | −869 |
| 09:26 | Catholyte | | 85 | 9.9 | 4.77 | −889 |
| 09:43 | Catholyte | pump bottom | −804 | 11.1 | 6.61 | |
| 10:21 | Catholyte | drain | 5 | 11.1 | 6.35 | −809 |
| 10:23 | Catholyte | | 18 | 11.1 | 6 | −822 |
| 10:24 | Catholyte | pump bottom | −804 | 11.1 | 6.61 | |
| 10:42 | Catholyte | drain | 50 | 11.1 | 6 | −854 |
| 10:45 | Catholyte | pump top + drain | −804 | 11.1 | 6.61 | |
| 10:48 | Catholyte | drain | 9 | 11.2 | 6.39 | −813 |
| 10:52 | Catholyte | | −3 | 11.3 | 6.32 | −801 |
| 11:00 | Catholyte | | 32 | 11.1 | 5.51 | −836 |
| 11:07 | Catholyte | | 35 | 10.7 | 5.03 | −839 |
| 11:12 | Catholyte | | 54 | 10 | 5.29 | −858 |
| 11:15 | Catholyte | | 184 | 9.7 | 4.18 | −988 |
| 11:20 | Anolyte | pump top + drain | 935 | 6.6 | 5.15 | |
| 11:22 | Anolyte | drain | 295 | 9.9 | 4.98 | 640 |
| 11:28 | Anolyte | | 274 | 9.7 | 5.26 | 661 |
| 11:38 | Anolyte | | 334 | 9.2 | 5.26 | 601 |
| 11:47 | Anolyte | | 256 | 9.5 | 5.26 | 679 |

TABLE 6-continued

Changes in the physiochemical attributes of the ECA solutions applied to a GAC vessel over time
Changes in physiochemical parameters of Catholyte and Anolyte solutions when introduced into a Granular Activated Charcoal column over time

| Time | Solution type | Activity | ORP | pH | EC | Δ ORP Feed-Effluent |
|------|---------------|----------|-----|-----|------|-----|
| 11:49 | Anolyte | pump top, no drain | 935 | 6.6 | 5.15 | |
| 12:15 | Anolyte | drain | 215 | 9 | 5.21 | 720 |
| 12:21 | Anolyte | | 245 | 9 | 4.93 | 690 |
| 12:30 | Anolyte | pump bottom | 935 | 6.6 | 5.15 | |
| 13:06 | Anolyte | Pump top | 935 | 6.6 | 5.15 | |
| 13:20 | Anolyte | | 844 | 7.4 | 5.19 | 91 |
| 13:23 | Anolyte | | 792 | 7.5 | 5.15 | 143 |
| 13:28 | Anolyte | | 391 | 8.6 | 5.2 | 544 |
| 13:35 | Anolyte | pump bottom | 935 | 6.6 | 5.15 | |
| 14:06 | Anolyte | Pump top | 935 | 6.6 | 5.15 | |
| 14:18 | Anolyte | drain | 843 | 7.5 | 5.27 | 92 |
| 14:22 | Anolyte | steep | 831 | 7.4 | 5.24 | 104 |

Legend:
ORP—Oxidation Reduction Potential (mV—milliVolts),
EC—Electrical Conductivity (mS/cm—milliSiemens per centimeter)

Conclusion

It was demonstrated that the elevated Oxidation Reduction Potential (ORP) of the electrochemically activated Catholyte and Anolyte solutions, when applied as a tandem and sequential intervention to Granular Activated Charcoal (GAC) filtration columns, has the capacity to selectively manipulate the surface free energy charge on the surfaces and within the pores of the charcoal granules used for filtration and adsorption in beverage processing and packaging plants, as well as in other applications. This capacity serves to assist in the regeneration of the absorption characteristics of the granules as well as to substantially reduce the microbial burden both on the surfaces as well as within the pores of the granules.

EXAMPLE 5

Flavor Neutralization Capacity of ECA Solutions

It has further been discovered in accordance with the present invention that anolyte solutions can surprisingly provide an added benefit in that, in addition to its broad based antimicrobial efficacy, anolyte is able simultaneously to oxidize residual flavorant molecules and synthetic ingredient residues from manufacturing and packaging equipment.

The trial involved an organoleptic and calorimetric appraisal of the capacity of ECA solutions to eliminate persistent and robust flavor fingerprints from packaging equipment in a carbonated beverage plant.

The change from one particularly persistent and robust flavor type (pineapple based) to a standard cola flavor or soda water based product, demonstrated a complete elimination of residual carry-over of the flavorant substance after exposure to the ECA solutions.

Additionally, in-vitro testing with a range of commercial synthetic flavor molecules (Cranbrook Flavors) including Apple (MJ3116), Chemy (MJ2381), Raspberry (MJ3102), Blackcurrent (MJ1115), Pineapple (MJ2082), Bubblegum (MG1250) and Strawberry (MJ2507) all demonstrated effective neutralization in the ECA solutions spiked with the flavor molecules.

Conclusion: ECA anolyte solutions have the ability to neutralize persistent and robust flavor molecules.

EXAMPLE 6

An ECAW anolyte product was continuously dosed into well water used for beer production. During the course of the trial, the concentrated anolyte used in the test was maintained at a pH of about 6.5±0.5, an ORP (millivolts) of 900±50, and an electrical conductivity (mSiemens/cm) of 5.5±0.5. The resulting treated well water had an anolyte concentration of 0.5% by volume, a pH of 6.5±0.5, an ORP of 500±50, and an electrical conductivity of 0.2±0.05.

After steady state conditions were achieved, the treated well water was rendered microbe free. The treated well water was used as an actual ingredient for beer production. No adverse effects from the use of the treated water were detected in the taste, character, color or other characteristics of the beer product.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within this invention as defined by the claims.

What is claimed is:

1. A method of rehabilitating and disinfecting a granular activated charcoal bed used for purifying water wherein said granular activated charcoal bed is located in a vessel other than an electrochemical activation system and said method is conducted without passing an electrical current through said granular activated charcoal bed, said method comprising the non-simultaneous steps of:
    (a) contacting said granular activated charcoal bed with an electrochemically-activated water catholyte solution and
    (b) contacting said granular activated charcoal bed with an electrochemically-activated water anolyte solution,
    wherein steps (a) and (b) are performed in a manner effective to cause an amount of electrostatically bound material to be released from said granular activated charcoal bed and to neutralize free-floating and granular adherent microbes,
    prior to contacting said granular activated charcoal bed, said electrochemically-activated water catholyte solution and said electrochemically-activated water anolyte solution have each been produced in an electrochemical activation system by electrochemical activation of an aqueous salt solution comprising not more than 9 grams of salt per liter of water, said salt being sodium chloride, potassium chloride, or a combination thereof,
    when in undiluted form, said electrochemically-activated water catholyte solution has a negative oxidation-reduction potential of at least $^-110$ mV and a pH in a range of from about 8 to about 13, and
    when in undiluted form, said electrochemically-activated water anolyte solution has a positive oxidation-reduction potential of at least $^+650$ mV and a pH in a range of from about 4.5 to about 7.5.

2. The method of claim 1 wherein said negative oxidation-reduction potential of said electrochemically-activated water catholyte solution is at least $^-700$ mV.

3. The method of claim 1 wherein:
    said electrochemically-activated water catholyte solution is used in undiluted form for contacting said granular activated charcoal bed in step (a) and said electrochemically-activated water anolyte solution is used in undiluted form for contacting said granular activated charcoal bed in step (b).

4. The method of claim 1 wherein:
said electrochemically-activated water anolyte solution has a beginning oxidation-reduction potential prior to contacting said granular activated charcoal bed;
said beginning oxidation-reduction potential is a positive mV oxidizing value;
said electrochemically-activated water anolyte solution has a spent oxidation-reduction potential after being used for contacting said granular activated charcoal bed; and
step (b) comprises the steps of:
(i) determining said beginning oxidation-reduction potential of said electrochemically-activated water anolyte solution,
(ii) contacting said granular activated charcoal bed with said electrochemically-activated water anolyte solution,
(iii) determining said spent oxidation-reduction potential of said electrochemically-activated water anolyte solution after step (ii) and
(iv) repeating steps (ii) and (iii) at least until said spent oxidation-reduction potential of said electrochemically-activated water anolyte solution determined in step (iii) is a positive mV oxidizing value which is not more than 544 mV less than said beginning oxidation-reduction potential of said electrochemically-activated water anolyte solution.

5. The method of claim 4 wherein said beginning oxidation-reduction potential of said electrochemically-activated water anolyte solution is at least $^{+}650$ mV.

6. The method of claim 4 wherein, in step (iv), steps (ii) and (iii) are repeated at least until said spent oxidation-reduction potential of said electrochemically-activated water anolyte solution determined in step (iii) is not more than 143 mV less than said beginning oxidation-reduction potential of said electrochemically-activated water anolyte solution.

7. The method of claim 4 wherein, in step (iv), steps (ii) and (iii) are repeated at least until said spent oxidation-reduction potential of said electrochemically-activated water anolyte solution determined in step (iii) is not more than 104 mV less than said beginning oxidation-reduction potential of said electrochemically-activated water anolyte solution.

8. The method of claim 1 wherein step (b) is conducted at least twice such that:
said electrochemically-activated water anolyte solution is at least once delivered to said granular activated charcoal bed in a substantially normal operating flow direction and
said electrochemically-activated water anolyte solution is at least once delivered to said granular activated charcoal bed in a reverse flow direction which is substantially opposite said substantially normal operating flow direction.

9. The method of claim 1 wherein step (a) is conducted at least twice such that:
said electrochemically-activated water catholyte solution is at least once delivered to said granular activated charcoal bed in a substantially normal operating flow direction and
said electrochemically-activated water catholyte solution is at least once delivered to said granular activated charcoal bed in a reverse flow direction which is substantially opposite said substantially normal operating flow direction.

* * * * *